(12) United States Patent
Vargas

(10) Patent No.: US 8,821,429 B2
(45) Date of Patent: Sep. 2, 2014

(54) INTRAGASTRIC IMPLANT DEVICES

(75) Inventor: Jaime Vargas, Redwood City, CA (US)

(73) Assignee: IBIS Medical, Inc., Redwood City, CA (US)

( * ) Notice: Subject to any disclaimer, the term of this patent is extended or adjusted under 35 U.S.C. 154(b) by 664 days.

(21) Appl. No.: 12/568,899

(22) Filed: Sep. 29, 2009

(65) Prior Publication Data

US 2010/0049224 A1 Feb. 25, 2010

Related U.S. Application Data

(63) Continuation of application No. PCT/US2008/004207, filed on Mar. 31, 2008.

(60) Provisional application No. 60/908,902, filed on Mar. 29, 2007.

(51) Int. Cl.
*A61B 17/00* (2006.01)
*A61F 5/00* (2006.01)
*A61F 2/04* (2013.01)
*A61B 17/12* (2006.01)
*A61M 25/04* (2006.01)

(52) U.S. Cl.
CPC ............. *A61F 5/0076* (2013.01); *A61F 5/0036* (2013.01); *A61F 5/0073* (2013.01); *A61F 5/003* (2013.01); *A61F 5/0079* (2013.01); *A61F 5/0003* (2013.01); *A61F 5/0013* (2013.01); *A61F 2002/045* (2013.01); *A61B 17/12099* (2013.01); *A61B 17/12136* (2013.01); *A61M 25/04* (2013.01); *A61M 2210/1042* (2013.01); *A61M 2210/1053* (2013.01); *A61M 2210/1057* (2013.01); *A61M 2210/106* (2013.01)
USPC ............. 604/8; 604/93.01; 604/104; 604/264; 623/11.11; 623/23.64; 623/23.65; 623/23.67; 623/23.7; 606/108

(58) Field of Classification Search
CPC . A61F 5/003; A61F 2002/045; A61F 5/0033; A61F 5/0036; A61F 5/0073; A61F 5/0076; A61F 5/0079; A61F 2/02; A61F 2/04; A61F 5/0003; A61F 5/0013; A61B 17/00535; A61B 2017/00539; A61B 17/12099; A61B 17/12136; A61B 2017/00818; A61B 2017/00827; A61M 25/04; A61M 2210/1042; A61M 2210/1053; A61M 2210/1057; A61M 2210/106
USPC .............. 604/8, 9, 264, 265, 270, 93.01, 104, 604/105, 106, 107, 108, 109; 623/11.11, 623/23.64, 23.65, 23.67, 23.68, 23.7, 9; 606/108
See application file for complete search history.

(56) References Cited

U.S. PATENT DOCUMENTS 4,485,805 A * 12/1984 Foster, Jr. ...................... 128/898
4,648,383 A    3/1987 Angelchik (Continued)

FOREIGN PATENT DOCUMENTS

WO     2010/074712 A2    7/2010

OTHER PUBLICATIONS http://www.macmillandictionary.com/dictionary/american/rigid. Accessed Tuesday, Sep. 18, 2012.*

(Continued)

*Primary Examiner* — Adam Marcetich
(74) *Attorney, Agent, or Firm* — Kilpatrick Townsend & Stockton LLP; Kenneth R. Shurtz, Esq.

(57) ABSTRACT

An intragastric implant comprises an anchor and a therapeutic device or a diagnostic device. The anchor is adapted to extend between the fundus and the pyloric valve of a stomach, to be retained without attachment to the stomach wall, and to anchor the device within the stomach with a relatively stable position and orientation. The therapeutic or diagnostic device is adapted to extend from the esophagus or stomach to the intestines or stomach. The therapeutic or diagnostic device, when extending into the esophagus, will be slidably received through the gastroesophageal junction and, when extending into the intestines, will be slidably received in the pyloric valve.

45 Claims, 19 Drawing Sheets

(56) References Cited

U.S. PATENT DOCUMENTS

| | | | |
|---|---|---|---|
| 4,694,827 A | | 9/1987 | Weiner et al. |
| 4,878,905 A | | 11/1989 | Blass |
| 4,899,747 A | * | 2/1990 | Garren et al. ............ 606/192 |
| 4,925,446 A | | 5/1990 | Garay et al. |
| 5,306,300 A | | 4/1994 | Berry |
| 5,401,241 A | * | 3/1995 | Delany ............ 604/43 |
| 5,820,584 A | | 10/1998 | Crabb |
| 5,868,141 A | | 2/1999 | Ellias |
| 6,629,987 B1 | | 10/2003 | Gambale et al. |
| 7,033,384 B2 | | 4/2006 | Gannoe et al. |
| 7,320,696 B2 | | 1/2008 | Gazi et al. |
| 7,803,195 B2 | | 9/2010 | Levy et al. |
| 7,892,214 B2 | | 2/2011 | Kagan et al. |
| 2002/0161341 A1 | | 10/2002 | Stinson et al. |
| 2003/0040804 A1 | | 2/2003 | Stack et al. |
| 2003/0040808 A1 | * | 2/2003 | Stack et al. ............ 623/23.65 |
| 2003/0109935 A1 | * | 6/2003 | Geitz ............ 623/23.65 |
| 2003/0199991 A1 | * | 10/2003 | Stack et al. ............ 623/23.65 |
| 2004/0092974 A1 | * | 5/2004 | Gannoe et al. ............ 606/153 |
| 2004/0267378 A1 | * | 12/2004 | Gazi et al. ............ 623/23.67 |
| 2005/0049718 A1 | * | 3/2005 | Dann et al. ............ 623/23.65 |
| 2005/0080431 A1 | | 4/2005 | Levine et al. |
| 2005/0096750 A1 | | 5/2005 | Kagan et al. |
| 2005/0192614 A1 | | 9/2005 | Binmoeller |
| 2005/0197714 A1 | * | 9/2005 | Sayet ............ 623/23.65 |
| 2005/0228504 A1 | | 10/2005 | Demarais |
| 2005/0267596 A1 | * | 12/2005 | Chen et al. ............ 623/23.67 |
| 2005/0273060 A1 | | 12/2005 | Levy et al. |
| 2006/0064120 A1 | * | 3/2006 | Levine et al. ............ 606/153 |
| 2006/0142731 A1 | | 6/2006 | Brooks |
| 2006/0178691 A1 | * | 8/2006 | Binmoeller ............ 606/191 |
| 2006/0190019 A1 | * | 8/2006 | Gannoe et al. ............ 606/153 |
| 2007/0083271 A1 | | 4/2007 | Levine et al. |
| 2007/0149994 A1 | * | 6/2007 | Sosnowski et al. ............ 606/192 |
| 2007/0198074 A1 | | 8/2007 | Dann et al. |
| 2007/0250020 A1 | * | 10/2007 | Kim et al. ............ 604/264 |
| 2009/0118749 A1 | | 5/2009 | Shalon et al. |
| 2010/0160933 A1 | | 6/2010 | Krueger et al. |
| 2010/0256775 A1 | | 10/2010 | Belhe et al. |
| 2010/0286628 A1 | | 11/2010 | Gross |
| 2011/0000496 A1 | | 1/2011 | Priplata et al. |
| 2011/0009690 A1 | | 1/2011 | Belhe et al. |
| 2011/0040232 A1 | | 2/2011 | Magal |
| 2011/0046537 A1 | | 2/2011 | Errico et al. |
| 2012/0004676 A1 | | 1/2012 | Vargas |
| 2013/0079603 A1 | | 3/2013 | Vargas |

OTHER PUBLICATIONS

International Search Report and Written Opinion of The International Searching Authority issued in PCT/US12/57288 on Feb. 8, 2013, 14 pages.

International Preliminary Report on Patentability issued in PCT/US2011/030210 on Oct. 11, 2012, 6 pages.

PCT International Search Report and Written Opinion of May 27, 2011 for application PCT/US2011/030210.

* cited by examiner

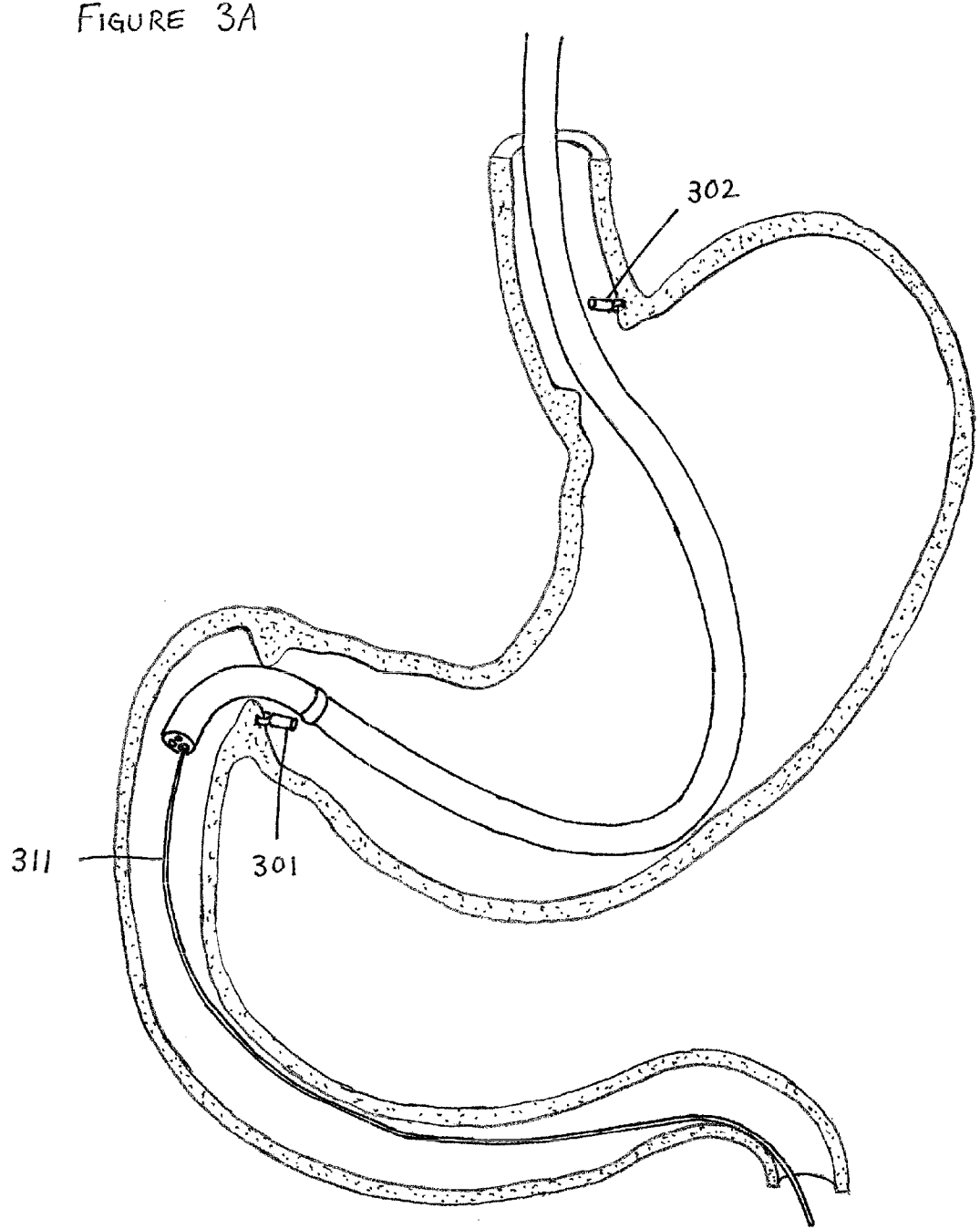

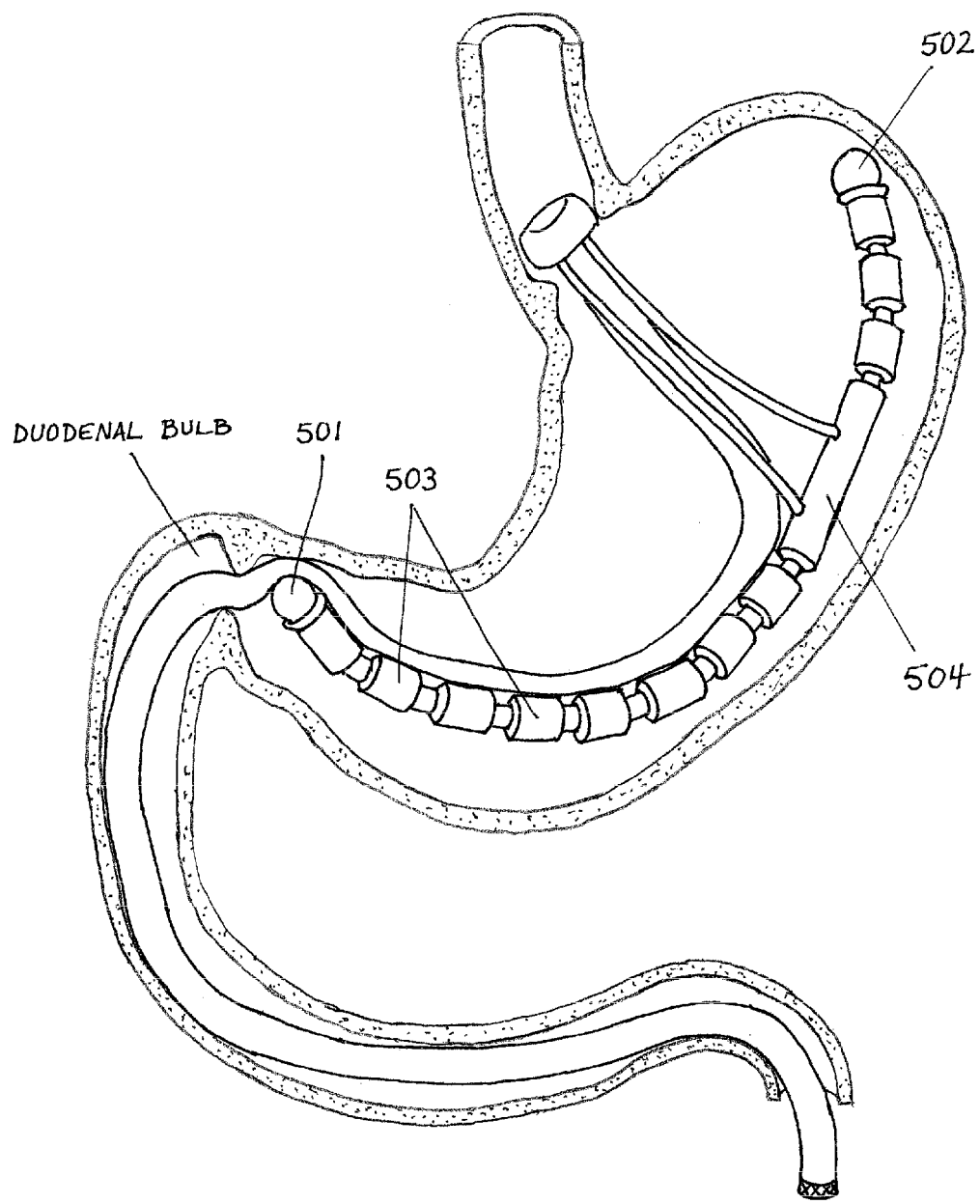

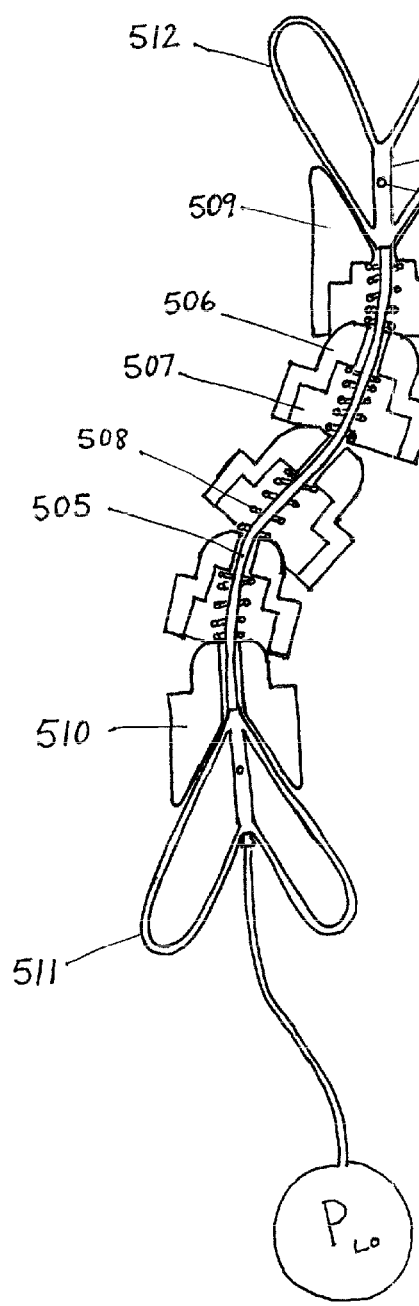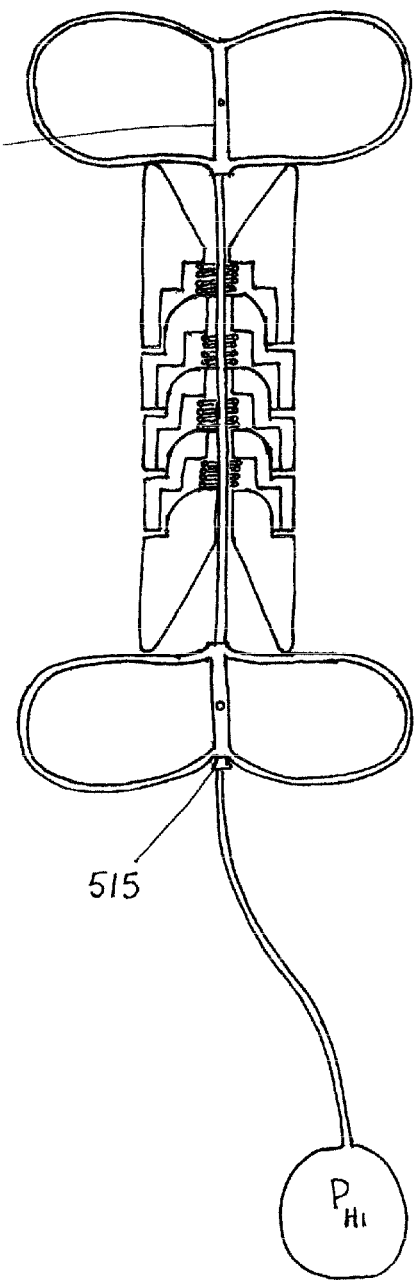

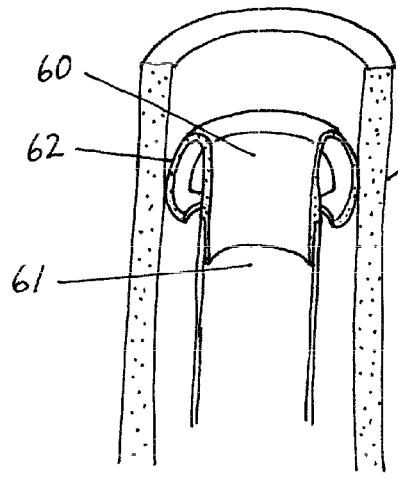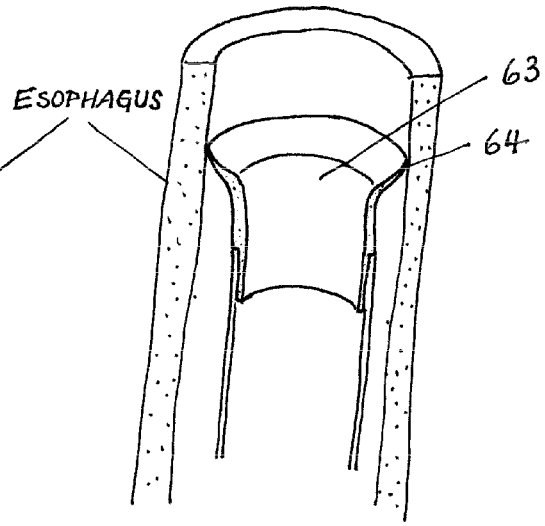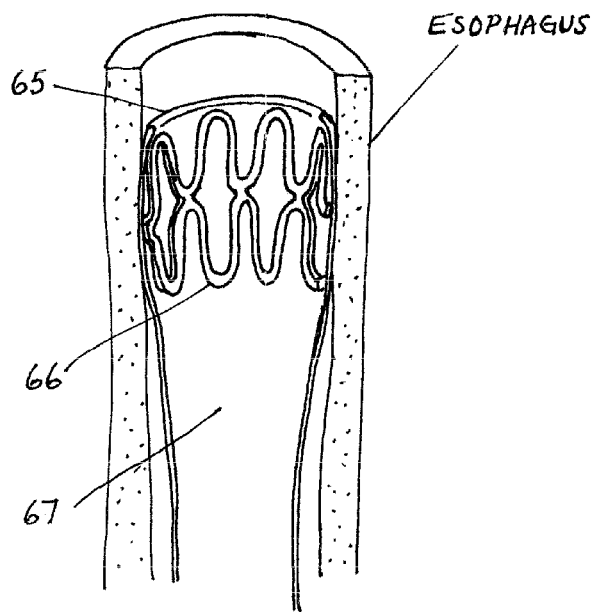

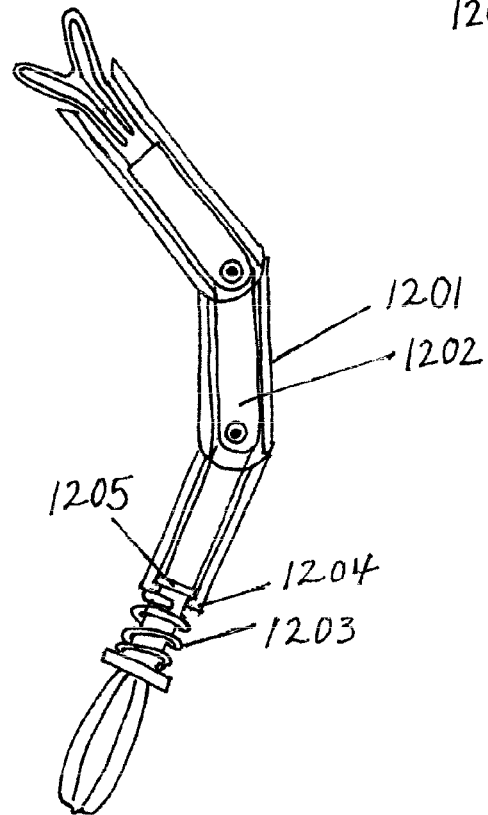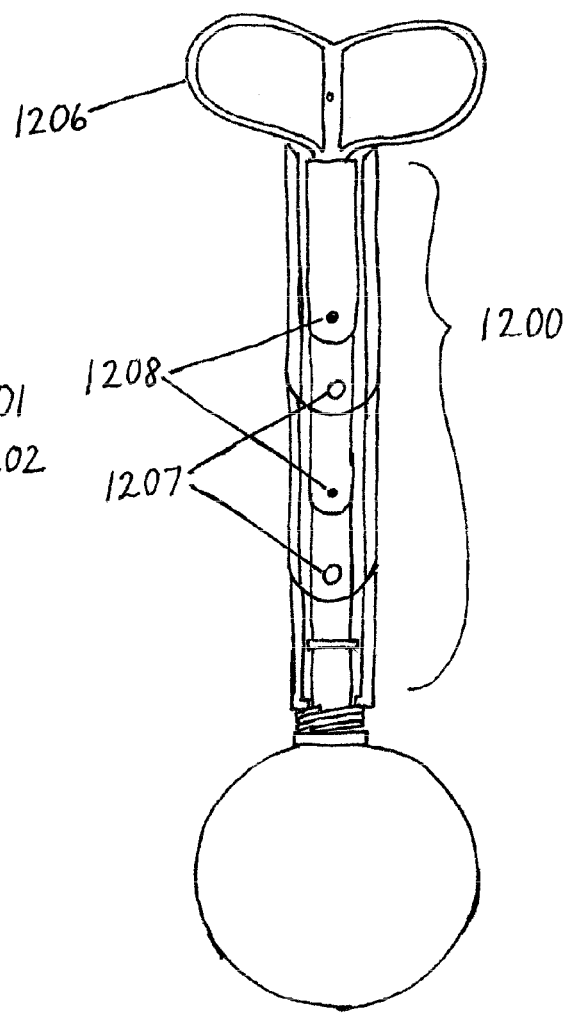

INTRAGASTRIC IMPLANT DEVICES

This application is a continuation of International Patent Application No. PCT/US2008/004207, filed Mar. 31, 2008 and designating the United States, which International application claims the benefit of U.S. Provisional Patent Application No. 60/908,902, filed Mar. 29, 2007, the entire disclosures of which are incorporated herein by reference.

BACKGROUND OF THE INVENTION

The invention disclosed herein enables anchoring of therapeutic or diagnostic devices, such as for example bariatric sleeves, within the stomach with a relatively stable position and orientation. The system can supplement such current weight reduction technology as intragastric balloons and gastric banding as well as bariatric surgeries such as Roux-en-Y gastric bypass.

Roux-en-Y gastric bypass has proven an especially effective weight-reduction surgery, likely because it acts through multiple mechanisms. By reducing the effective size of the stomach the surgery reduces oral intake's exposure to gastric digestive juices and promotes early satiety by leaving a smaller residual stomach to fill. In bypassing the ampulla of Vater and a length of proximal small intestine the surgery delays the action of biliary and digestive enzymes on food particles while reducing the length of small bowel exposed to nutrients.

Current bariatric surgery procedures, while proven effective and beneficial for patients, are highly invasive, result in permanent changes to the patient's digestive tract, and carry a substantial risk of surgical complications or death. As a consequence of the risk, bariatric surgery is generally indicated only for the morbidly obese, body mass index (BMI) 40 or greater, or for the moderately obese (BMI>35) with substantial obesity-related comorbidities such as diabetes and hypertension.

BRIEF SUMMARY OF THE INVENTION

Prior to this invention, gastric anchoring methods have required stapling, suturing, or other modification of the anatomy to hold a device in place. In contrast, the invention described herein exploits asymmetric geometry of gastric anatomy to maintain a gastric implant in a relatively fixed position within the gastrointestinal tract without attachment to the gastric wall. Specifically, the present invention is directed to a gastric implant that comprises an intragastric anchor and a therapeutic or diagnostic device coupled to the anchor. The intragastric anchor of the invention limits the movements of any device attached to it to the displacement available to the anchor within the stomach. In one embodiment, the intragastric anchor has an elongate shape extending along the long axis of the stomach substantially from the antrum to the fundus such that displacement of the anchor along the long axis due to gastric contractility or other causes is limited by the gastric anatomy of the fundus and pylorus. Similarly, the elongate anchor is configured to be longer than the transverse width of the stomach and thus too long to be flipped end over end within the stomach by gastric contractility. Thus, the intragastric anchor provides a relatively stable platform on which to anchor bariatric or other therapeutic or diagnostic devices. Once deployed within the stomach, the anchor is configured to be larger than the pyloric valve to prevent its passing out of the stomach and into the small bowel. This configuration enables the intragastric anchor to maintain a relatively fixed position and orientation within the gastrointestinal tract. Additionally, an extension from the anchor into the esophagus may be present, which defines a plane such that the anchor may also prevent rotation within the stomach. The present invention is further directed to a method for anchoring a therapeutic device or a diagnostic device within the stomach in a relatively fixed position, that is with a relatively stable position and orientation, while being free from attachment to the stomach wall, the method comprising positioning an anchor according to the invention in the stomach of a patient between the fundus and the pyloric valve; and coupling a therapeutic device or a diagnostic device to the anchor.

Having secured the anchoring implant within the stomach, any number of devices may be attached to it. In one embodiment, the device is a therapeutic device. For example, a bariatric sleeve may be secured to extend from the esophagus to the jejunum, supported by a geometrically-fixed intragastric anchor. Similarly, a jejunal bypass sleeve extending from the pylorus into the jejunum may be supported by such an anchor. Also similarly, devices restricting gastric inflow and/or outflow may be supported by an intragastric anchor. Alternatively, a removable esophageal stent deliberately designed for sliding contact within the esophagus, so as to avoid hyperplastic tissue ingrowth, may be supported by the intragastric anchor. The combination of elongate intragastric anchor and sliding esophageal stent improves upon conventional stenting by avoiding the tendency of esophageal stents to migrate or to become unremovable through hyperplastic tissue ingrowth and scarring.

Similarly, diagnostic devices, such as for example a pH sensor, may be supported within the gastrointestinal tract by an intragastric anchor. By way of example, when configured to maintain a pH sensor within the esophagus, an intragastric anchor may include an esophageal extension, extending from the body of the anchor through the lower esophageal sphincter and into the esophagus, to support the sensor in a relatively fixed position within the esophagus. Since the esophagus serves to introduce oral intake into the stomach, the pH sensor is preferably held relatively apposed to the esophageal wall to avoid luminal blockage. Furthermore, since the intragastric anchor will move in a restricted fashion during normal gastric contractility and likewise move the pH sensor affixed to it, the pH sensor is preferably slidably coupled to the esophagus by an atraumatic sliding apposition structure. Regular sliding along the esophageal wall reduces the possibility of hyperplastic tissue ingrowth, minimizes pressure on healthy mucosa, and enhances the removability of the sensor. The combination of elongate intragastric anchor and sliding apposition structure improves upon stenting, stapling, suturing, and other fixation methods for implanted diagnostic devices by avoiding the tendency of such implants to migrate or to become unremovable through tissue ingrowth and scarring.

One application of the intragastric anchor revolves around bariatric therapy. A specific implementation described in this disclosure mimics the mechanisms by which Roux-en-Y gastric bypass surgery is thought to operate while avoiding surgical changes to the patient's anatomy. An anchored bariatric sleeve reduces the effective volume of the stomach and provides a mechanism for early satiety through stimulation of stretch receptors in the fundus, reduces exposure to gastric juices by bypassing the stomach, delays exposure to digestive enzymes by bypassing the ampulla of Veter, and reduces nutrient absorption by bypassing a section of the small bowel.

Configured to secure an anchored bariatric sleeve within the gastrointestinal tract, the intragastric anchor supports the proximal opening of the sleeve in the esophagus proximal to the gastroesophageal junction such that it does not migrate into the stomach. Since the intragastric anchor will move in a restricted fashion during normal gastric contractility and will likewise move the bariatric sleeve affixed to it, the proximal opening of the anchored bariatric sleeve is preferably slidably coupled to the esophagus by an atraumatic sliding esophageal seal. The combination of elongate intragastric anchor and sliding esophageal seal improves upon stenting, stapling, suturing, and other fixation methods by avoiding the tendency of gastrointestinal tract implants to migrate or to become unremovable through tissue ingrowth and scarring.

One embodiment of an anchored bariatric sleeve device includes a substantially axially noncompliant structure extending from the intragastric anchoring body into the esophagus. The relatively axially noncompliant esophageal extension supports the proximal opening of the bariatric sleeve and the sliding esophageal seal. The distal section of the bariatric sleeve extends into the small bowel. Such a device effectively duplicates the multiple therapeutic mechanisms of the Roux-en-Y gastric bypass.

The anchored bariatric sleeve is delivered to the target site either via a prepositioned guidewire or configured as an overtube slid over an endoscope. The device may include multiple radiopaque markers along its length to aid deployment under fluoroscopic guidance. For example, markers are placed at the distal end of the jejunal bypass tube, at the antral (distal) end of the intragastric anchor, at the fundal (proximal) end of the intragastric anchor, and at the sliding esophageal seal.

In a first specific aspect of the present invention, an intragastric implant comprises an elongate anchor adapted to extend substantially from the fundus to the pyloric valve in a patient, and a therapeutic or diagnostic device, such as a bariatric sleeve, coupled to the anchor. By "extends substantially from the fundus to the pyloric valve" is meant that the anchor may reach from the proximal stomach in the fundal area to the distal stomach in the antral area. The anchor may be shorter than the stomach but generally reaches from one end to the other, so that the ends sit in the antrum and fundus but do not necessarily contact the pylorus or the end of the fundus. The elongate anchor will usually be adapted to remain positioned in the stomach without the need for suturing, stapling, or other forms of attachment. The length and geometry of the anchor will typically be selected to assure that the anchor remains within the stomach without being ejected through the pyloric valve or otherwise adversely affecting the patient. The therapeutic or diagnostic device will be either fixedly or movably coupled to the anchor, and may be coupled at one or more points. In the case of a bariatric sleeve, the bariatric sleeve will be configured to act in a manner similar or analogous to the Roux-en-Y gastric bypass, typically having a central passage with an upper or proximal opening positionable in the esophagus and a lower or distal outlet positionable in the intestines, or in some instances within the stomach. The bariatric sleeve may have a variety of particular configurations: it may be either rigid, flexible, or have portions of each; it may be either straight, curved, or have other combination geometries; and/or it may comprise nestable, interlocking or hinged links in order to have a shape-lock configuration which facilitates introduction and subsequent reconfiguration within the stomach. The elongate anchor will usually have upper and lower atraumatic ends, where the atraumatic end may be a bulbous geometry, a looped structure, or the like.

The bariatric sleeve will usually have a resilient sliding seal at its proximal end, which is adapted to slide against or slidably engage the inner wall of the esophagus. The sliding seal may be an inflatable balloon or cuff structure, or it may be a resilient flared structure, or it may be a stented structure to provide a resilient opening force, or the like. Usually, the bariatric sleeve will also slidably extend through the pyloric valve so that both the upper and lower ends of the sleeves may move within the gastroesophageal junction and pyloric valve as the stomach changes positions.

In another aspect of the present invention, a method for treating obesity comprises positioning an anchor in the stomach of a patient. The anchor will typically be positioned between the fundus and the pyloric valve and will usually be free from attachment to the stomach wall. A bariatric sleeve is coupled to the anchor, and the anchor positions an upper opening of the sleeve in the esophagus and a lower outlet of the sleeve in the intestines or the stomach. The sleeve is slidably received through the gastroesophageal junction and the pyloric valve, and the opening of the sleeve is preferably slidably disposed against a wall of the esophagus to inhibit food bypass.

BRIEF DESCRIPTION OF THE DRAWINGS

FIG. 3A is a view of a sectioned stomach and small bowel with gastroscope, guidewire and pyloric and gastroesophageal junction marker clips.

FIG. 5A is a view of a sectioned stomach with a linked intragastric anchor in a relaxed state.

FIG. 5C is a sectioned view of a balloon-tensioned linked intragastric anchor detailing link and balloon structure with balloons deflated.

FIG. 5D is a sectioned view of a balloon-tensioned linked intragastric anchor detailing link and balloon structure with balloons inflated.

FIG. 6A is a sectioned view of a sliding esophageal seal with a curved contact surface.

FIG. 6B is a sectioned view of a sliding esophageal seal with a tapered wiper contact surface.

FIG. 6C is a sectioned view of a sliding esophageal seal with a self-expanding scaffold.

FIG. 12A is a sectioned view of a balloon-tensioned linked intragastric anchor detailing link and balloon structure with balloons deflated.

FIG. 12B is a sectioned view of a balloon-tensioned linked intragastric anchor detailing link and balloon structure with balloons inflated.

DETAILED DESCRIPTION OF THE INVENTION

Figure 1:
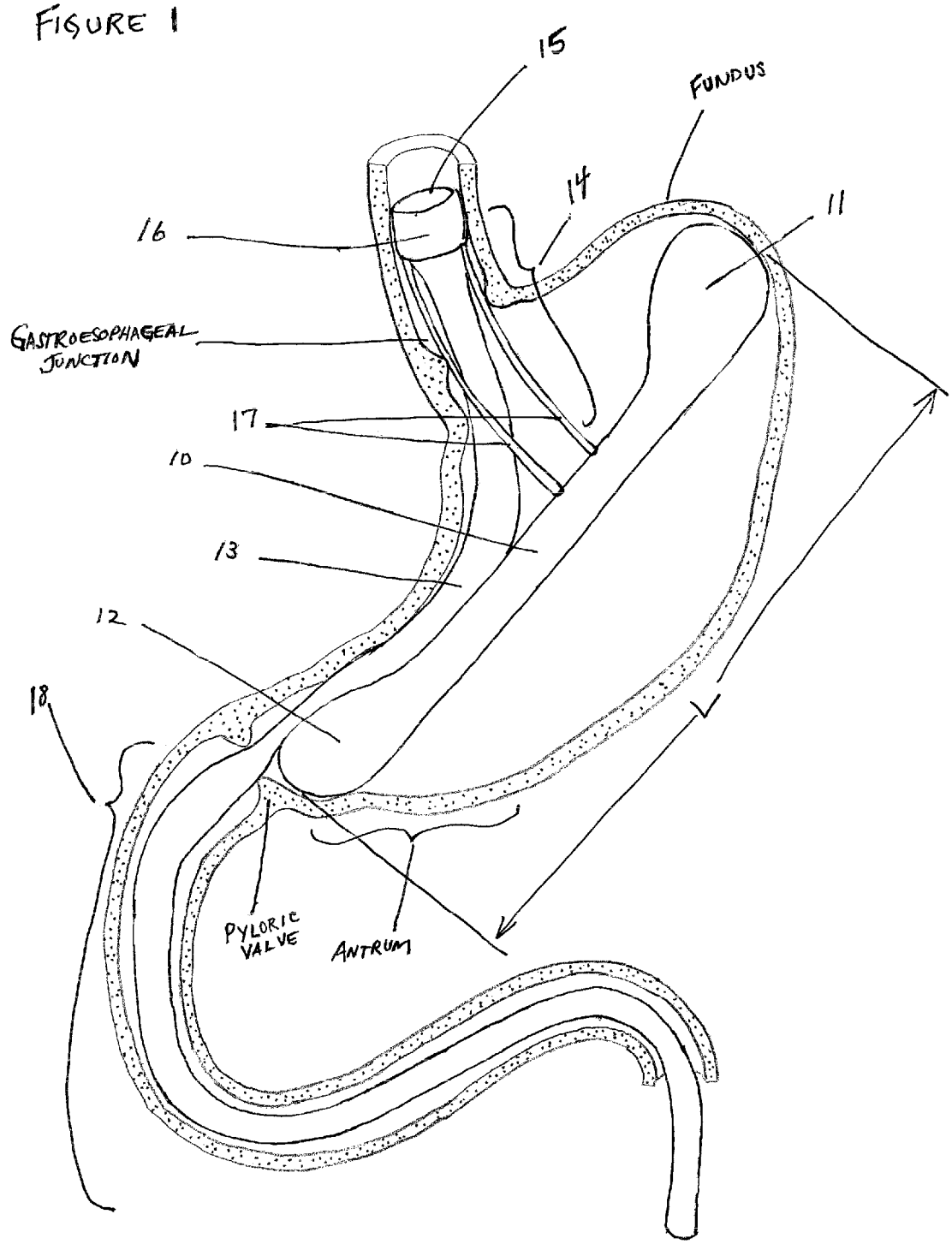
FIG. 1 is a diagrammatic view of an anchored bariatric bypass implant of the invention illustrating the major components.
Figure 11:
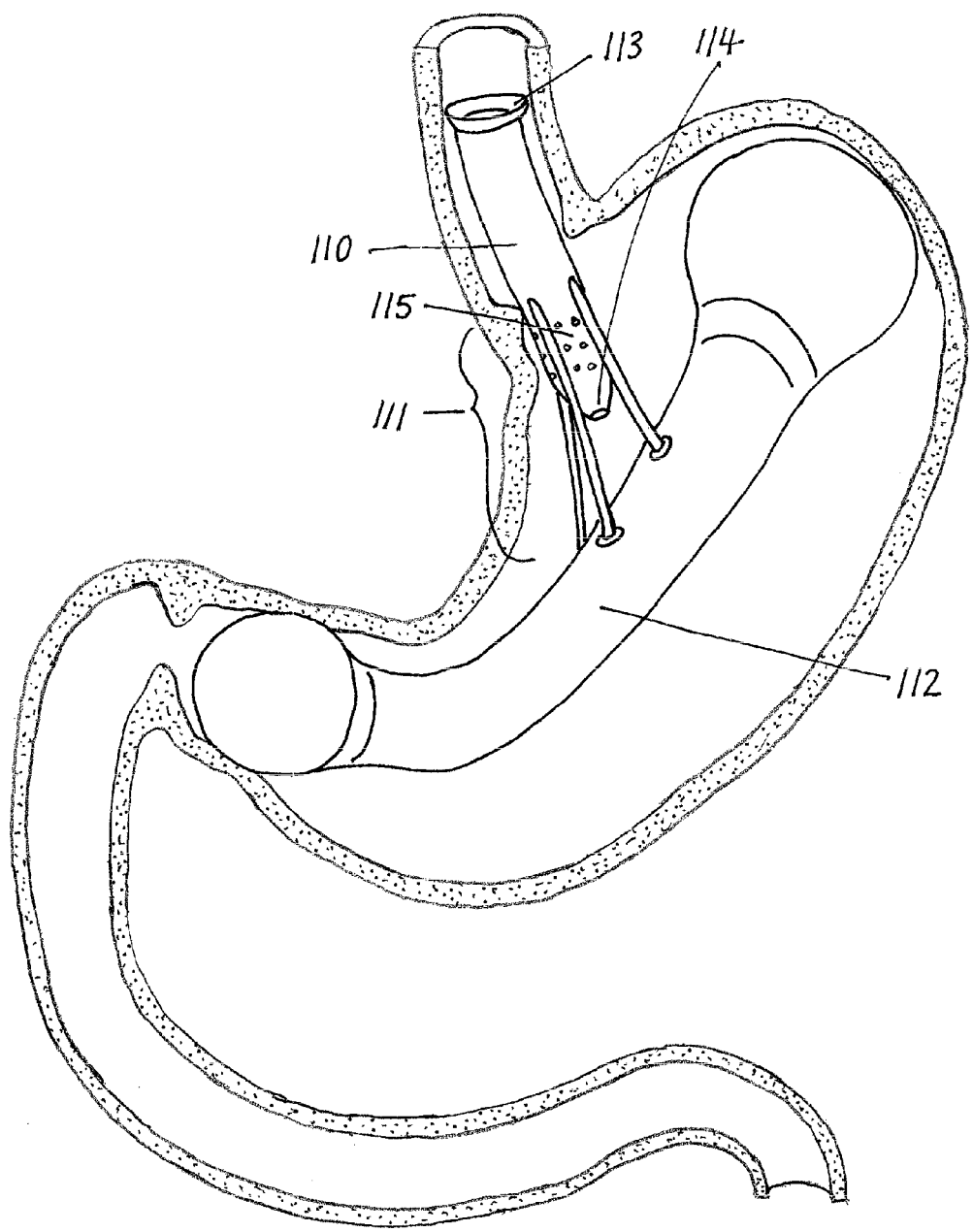
FIG. 11 is a view of a sectioned stomach with a gastric inflow restrictor supported by an intragastric anchor.

The intragastric anchor depicted in FIG. 1 includes a longitudinal anchoring body 10 that extends along the longest gastric axis from the antrum to the fundus. The anchoring body (10) may be substantially linear as shown in FIG. 1 such that it somewhat straightens the natural curvature of the stomach when deployed, or as shown in FIG. 11 the anchoring body (112) may be curved or bent to substantially follow the natural curvature of the stomach. Referring again to FIG. 1, the length L of the anchoring body 10 is greater than the stomach's largest flattened transverse diameter, thus preventing its end-to-end rotation within the stomach during normal gastric contractility. Length L should normally be in the range of from about 15 cm to about 50 cm, preferably from about 20 cm to about 40 cm, more preferably approximately 30 cm.

Referring to FIG. 1, blunted ends of the anchoring body prevent trauma to tissue as the anchor is pushed back and forth within the stomach by the antrum's grinding peristalsis. The blunt shape of the fundal bulb 11 distributes the substantial force exerted upon the fundus as the antrum squeezes the distal portion of the anchoring body and propels it proximally towards the fundus. The antral bulb 12 serves a similar force distribution purpose within the antrum and also serves to keep the anchoring body 10 from passing through the pyloric valve and into the small bowel. The antral bulb diameter should normally be in the range of from about 20 mm to about 50 mm, preferably from about 25 mm to about 40 mm, more preferably approximately 30 mm. An anchoring body configured to maintain its orientation within the stomach may serve to deliver drugs to specific areas of the stomach. By way of example the fundal bulb may include a drug-eluting coating with a drug specifically targeted to the fundus and the antral bulb may include a drug-eluting coating with a drug specifically targeted to the antrum.

Figure 2:
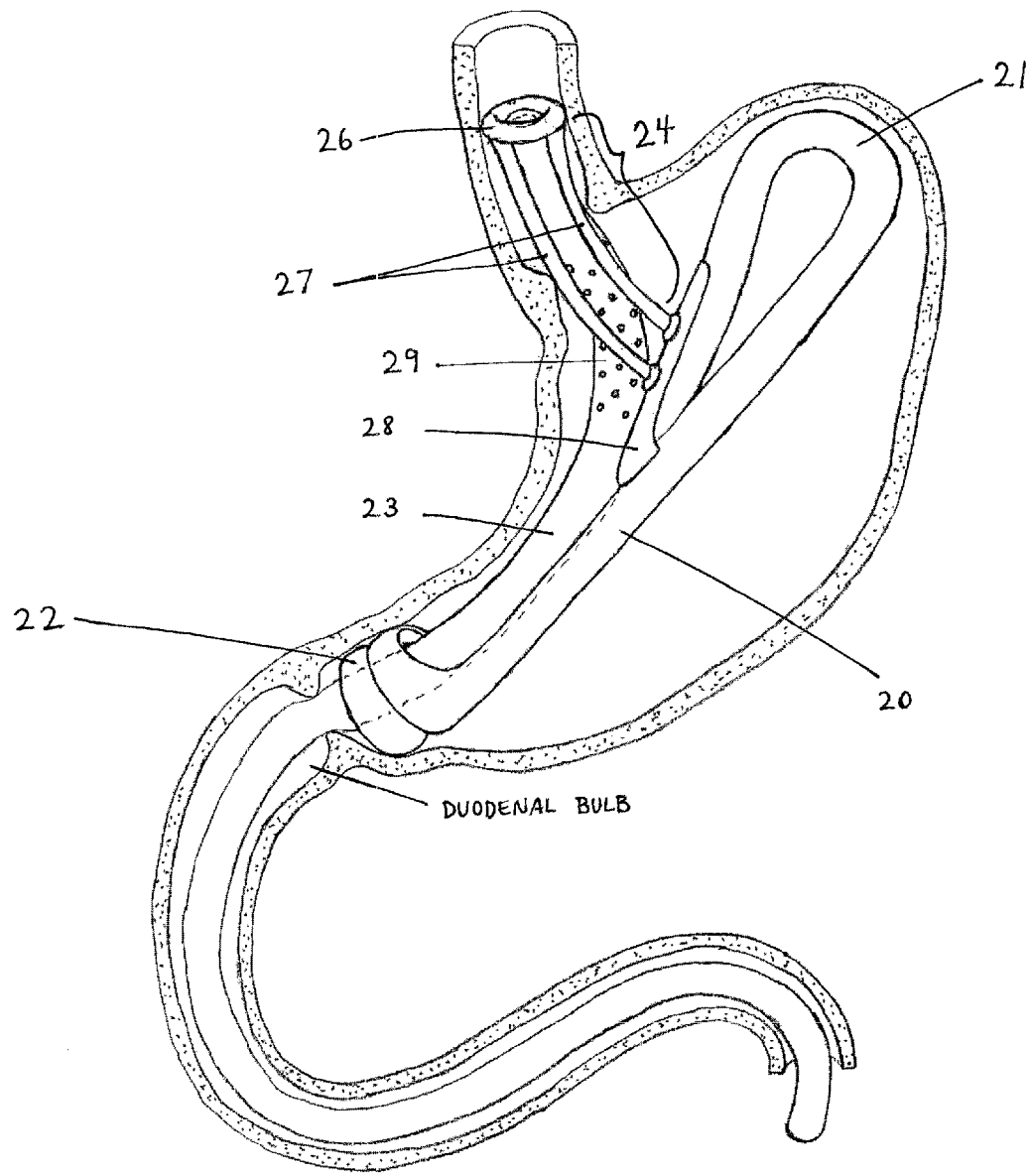
FIG. 2 is a view of an inflatable embodiment of an anchored bariatric implant in a sectioned stomach and small bowel.

The anchoring body may be implemented as a rigid or semirigid inflatable balloon structure. Referring to FIG. 2, in order to accommodate relatively high pressures in the main section of the anchoring body 20 and in the fundal bulb 21 and antral bulb 22, the anchoring body 20 may be formed of tubular sections shaped into appropriate dimensions for their respective functions. By way of example, rather than forming a fundal bulb with a large pressurized cross section, a relatively small diameter tubular balloon may be, as in FIG. 2, shaped into a fundal bulb 21 with a large sweeping shape and a relatively large radius of curvature so as to produce a relatively small surface pressure in the fundus. Also by way of example, rather than forming an antral bulb with a large pressurized cross-section, a relatively small diameter tubular balloon may be, as in FIG. 2, shaped into an antral bulb 22 with a curvature that at least partially wraps around and accommodates the bariatric sleeve 23 and with a sufficiently large diameter to prevent the antral bulb's passing through the pyloric valve while also producing a relatively small surface pressure on the antrum and pylorus.

Since an unintentional deflation resulting in a intragastric device passing through the pylorus and into the small bowel might cause an obstruction, FIG. 2 shows a rigid element 28 whose length dimension is small enough to pass through the esophagus and into the stomach but that is long enough not to pass beyond the duodenal bulb or through the tight bends of the relatively fixed duodenum. The rigid element may also serve as an attachment point for an esophageal extension 24. Struts 27 may extend from the rigid element to support a sliding esophageal seal 26. The rigid element 28 should normally be approximately 5 cm to 20 cm in length, preferably approximately 10 cm, and may be included in any suitable portion of the intragastric anchor.

The intragastric anchor serves to anchor therapeutic or diagnostic devices, such as for example bariatric sleeves, in a relatively stable position within the gastrointestinal tract. Employed as an anchor for a bariatric sleeve running from the esophagus to the small bowel, the anchoring body in FIG. 1 is affixed to and supports at least a portion of the compliant intragastric section of the bariatric sleeve 13 as it runs along the anchoring body, thus preventing it from kinking. The antral bulb 12 may run alongside the distal intragastric section of bariatric sleeve 13 or, as shown in FIG. 2, the antral bulb 22 may partially or completely surround the bariatric sleeve 23 to maintain a patent sleeve lumen proximal to the pylorus. Referring again to FIG. 1, the anchoring body 10 leaves a substantial portion of the bariatric sleeve's surface exposed to the stomach such that peristalsis may squeeze it against the anchoring body and drive food contents distally through the pyloric valve and into the small bowel. A portion of the bariatric sleeve 13 may be configured to be sufficiently flexible for the pyloric valve to pinch it shut when closed. The anchoring body supports the proximal opening 15 of the bariatric sleeve and a sliding esophageal seal 16 via an esophageal extension 14 reaching from the anchor into the esophagus proximal to the lower esophageal sphincter. The esophageal extension transmits the forces of esophageal peristalsis to the anchoring body 10, thus resisting the tendency of peristalsis to push the opening of the bariatric sleeve into the stomach. Since normal stomach contraction and peristalsis will rock and shift the anchoring body within the stomach within a certain range, the esophageal extension must be long enough to prevent the sliding seal from being drawn into the stomach by these motions. The esophageal extension should normally be about 5 cm to about 40 cm long, preferably about 10 cm to about 30 cm long, more preferably approximately 20 cm in length. Since the esophageal extension and anchoring body together define a plane, the esophageal extension also serves to resist any tendency of the anchoring body to rotate around its long axis within the stomach. Such rotation might twist or kink the bariatric sleeve to cause a blockage.

In a presently preferred embodiment, the esophageal extension comprises at least one and more preferably at least three struts connecting the anchoring body to an esophageal seal. In another presently preferred embodiment, the struts are configured to have a long aspect ratio such that they are relatively rigid along the esophageal axis but flexible in the transverse plane such that the lower esophageal sphincter may deflect the struts sufficiently to seal normally while retaining sufficient axial rigidity to support the esophageal seal against esophageal peristalsis. As is shown in FIG. 2, the esophageal extension may also maintain in a relatively stable position a perforated or otherwise gastric juice-permeable section 29 of the bariatric sleeve. In a preferred embodiment, the perforated section 29 is maintained just distal to the gastroesophageal junction to mimic the gastric juice exposure of a surgically-created gastric pouch in that location. The esophageal extension may be implemented in many ways within the scope of this invention. In a fluid-inflatable embodiment of the anchored bariatric sleeve depicted in FIG. 2, the esophageal extension 24 may comprise one or more gas- or liquid-pressurized struts 27 connecting the anchoring body to the esophageal seal. Similarly the esophageal extension may comprise one or more non-inflatable elastomeric struts with axial stiffness and transverse flexibility. In another embodiment of the esophageal extension, an axially stiff but radially flexible mesh may take the place of the struts to support the esophageal seal while allowing radial compression of the lower esophageal sphincter. Alternately, in an implementation of a temporary gastric sleeve implant, an esophageal extension may completely or partially stent open the lower esophageal sphincter. As such, the esophageal extension may have significant radial as well as axial stiffness.

Figure 4A:
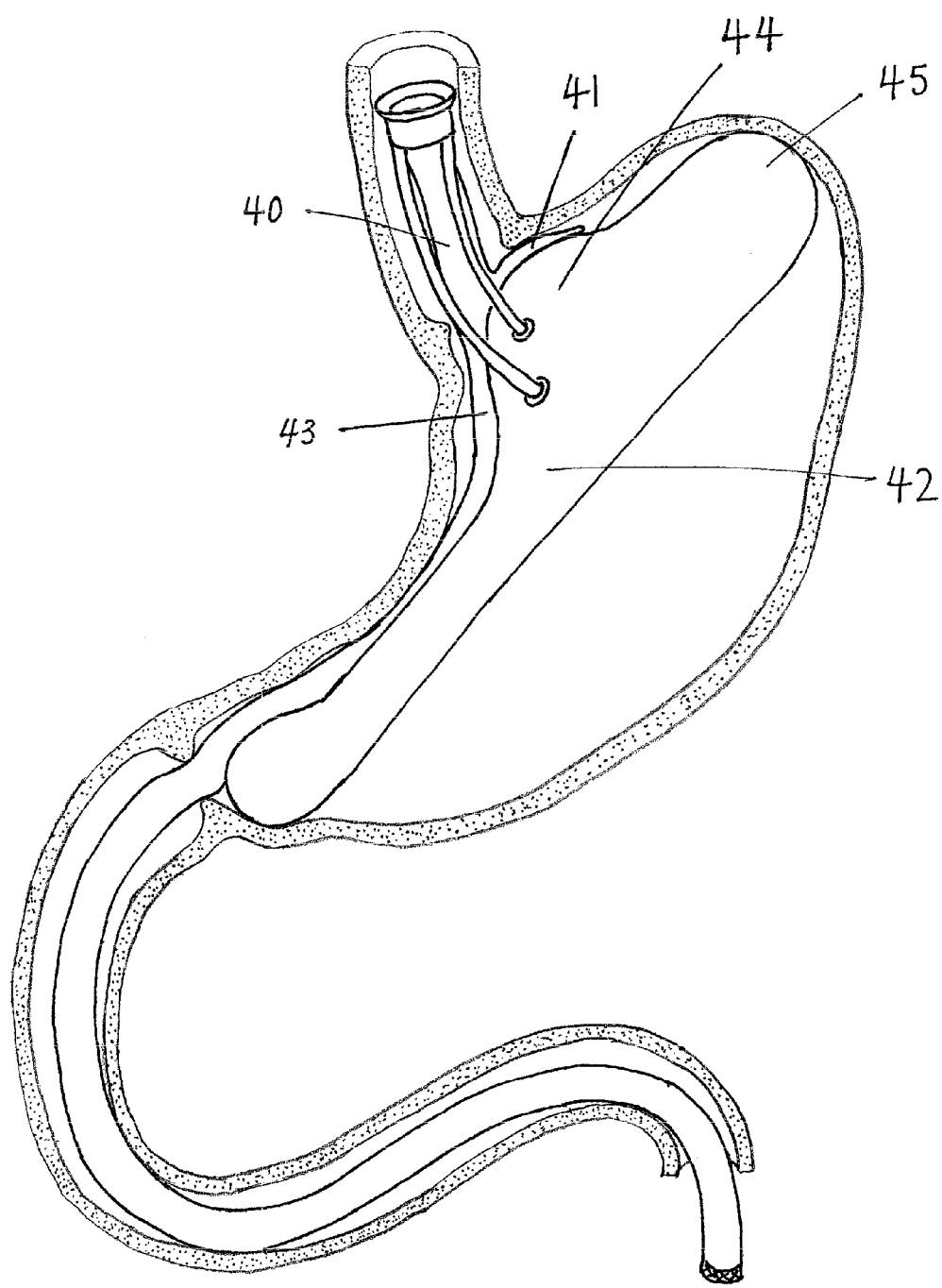
FIG. 4A is a view of a sectioned stomach with an anchored bariatric sleeve including a widened reservoir in the compressed state.
Figure 4B:
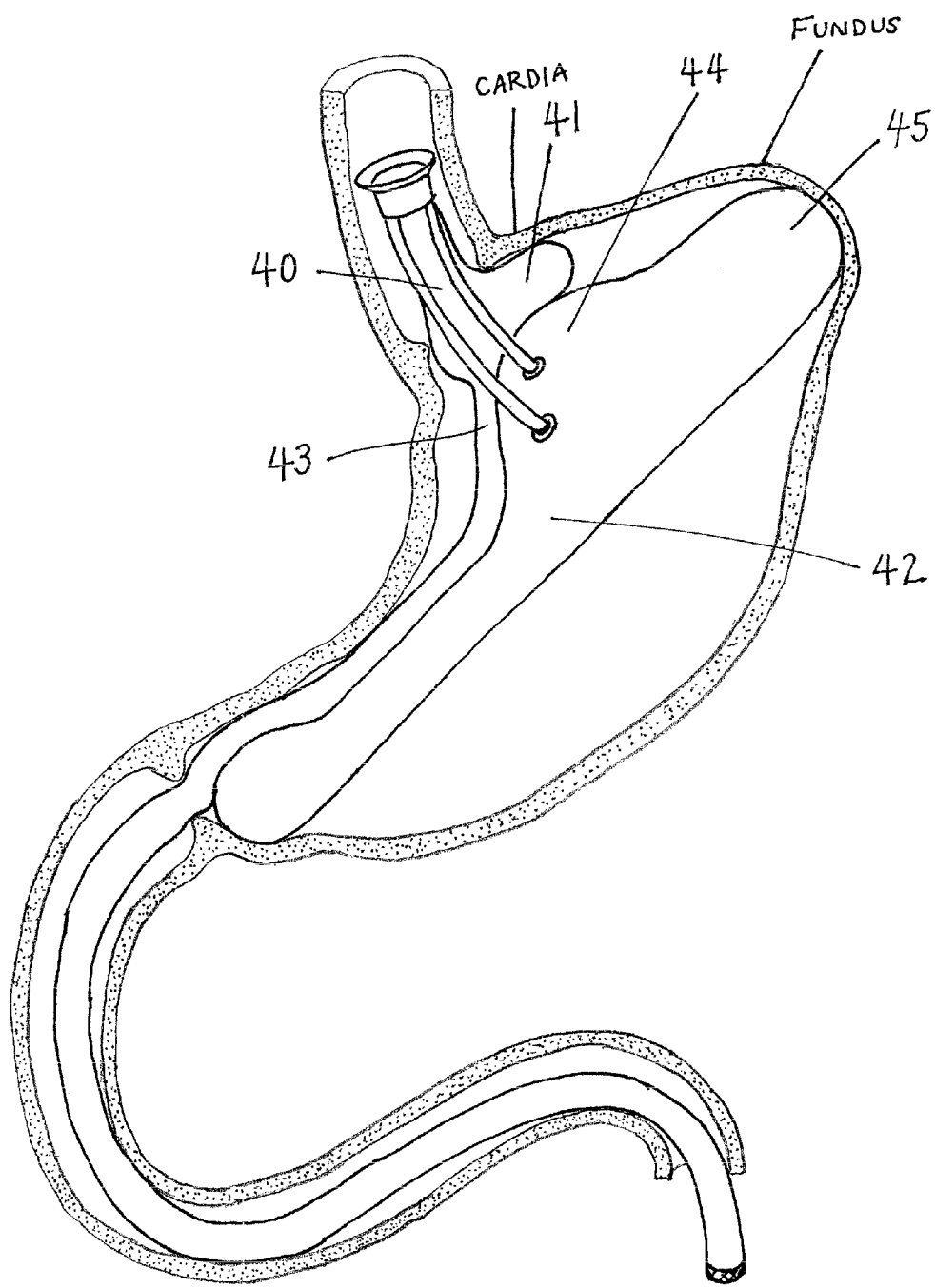
FIG. 4B is a view of a sectioned stomach with an anchored bariatric sleeve including a widened reservoir in the expanded state.

In order to mimic the early satiety mechanism of various restrictive bariatric surgical procedures, a bariatric sleeve 40 as shown in FIG. 4A may include a widened reservoir 41 just above the anchoring body 42 and a narrowed section 43 distal to the reservoir. Similar to the perforated section 29 of the bariatric sleeve shown in FIG. 2, the widened reservoir 41 may be perforated or otherwise made permeable to gastric juices so as to mimic the reduced exposure to gastric juices caused by stomach volume reducing surgeries such as Roux-en-Y gastric bypass. The narrowed section limits direct flow-through of solid oral intake into the duodenum and is analogous to the small-diameter gastricojejunostomy created in Roux-en-Y gastric bypass. Again referring to FIG. 4A, the anchoring body 42 is configured with a protrusion 44 that substantially fills the cardia portion of the stomach immediately distal to the lower esophageal sphincter and substantially compresses the empty reservoir 41. As the patient eats and the reservoir fills and expands as shown in FIG. 4B, the cardia is expanded while the anchoring body 42 is partially displaced from the cardia by the expanding reservoir 41, causing the fundal bulb 45 to press laterally outwards into the fundal wall. The reservoir normally has a volume of approximately 5 cc to 60 cc, preferably approximately 15 cc to 40 cc, more preferably approximately 30 cc. Actions on the cardial and fundal walls stimulate stretch receptors and serve as biofeedback mechanisms to promote satiety.

Figure 9:
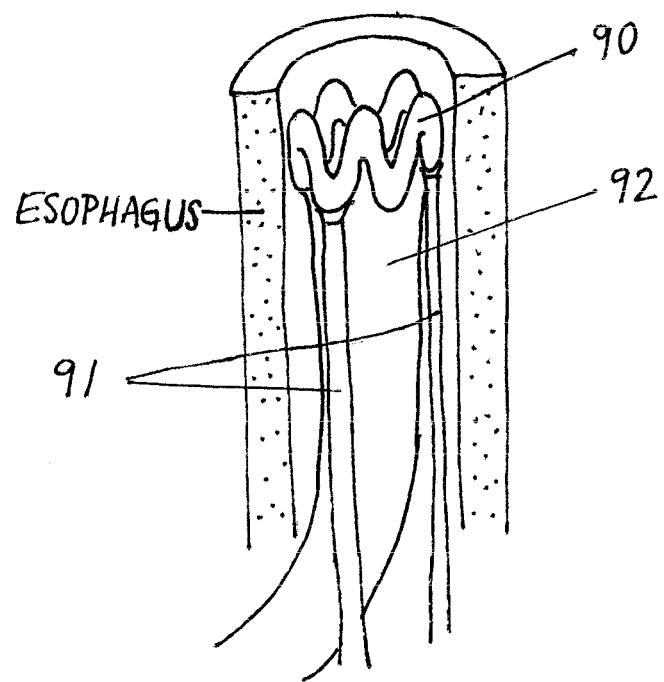
FIG. 9 is a view of a sectioned esophagus with a sinusoidal sliding esophageal seal.

Since normal stomach contraction and peristalsis will rock and shift the anchoring body within the stomach within a limited range, the proximal opening of the bariatric sleeve is best served by a sliding seal which can slide back and forth within the esophagus following the motions of the anchoring body while retaining the ability to direct most food particles into the proximal opening of the bariatric sleeve. The sliding seal may be implemented in a number of ways. As shown in FIG. 2, the sliding seal 26 may take the form of a rigid or semi-rigid inflatable smooth-edged structure that approximates the proximal opening of a gastric sleeve to the esophageal wall without fixing it in position and stays in light contact with the esophageal mucosa without enough force to damage the mucosa. Struts 27 support the sliding seal 26 against esophageal peristalsis and may serve as conduits for inflation fluid or gas, coupling the seal with the inflatable anchoring body 20. As shown in FIG. 9, an inflatable sliding seal 90 may be wavy or sinusoidal in form such that its diameter may expand or compress to accommodate a range of esophageal diameters as it holds open the proximal end of bariatric sleeve 92. Struts 91 support the sliding seal 90 axially against peristaltic esophageal contractility while allowing sufficient radial flexibility for the seal to accommodate a range of esophageal diameters. Alternately as shown in FIGS. 6A and 6B, the sliding seal may take the form of a compliant elastomeric wiper whose shape and durometer are selected for low friction and low normal force imparted to the esophageal wall while accommodating a range of esophageal diameters. The sliding seal 60 shown in section view in FIG. 6A holds open the proximal end of bariatric sleeve 61 and includes a compliant elastomeric sliding surface 62 radiused to present smooth curving edges to the esophagus both whether sliding proximally or distally. The sliding seal 63 shown in section view in FIG. 6B includes a tapered compliant elastomeric sliding surface 64 configured as a low-friction wiper. Similarly as shown in FIG. 6C, a proximal opening of the bariatric sleeve 67 may be configured for sliding with a radiused proximal edge 65 and may be propped open and held slidably apposed to the esophageal wall by a self-expanding scaffold 66 made of polymer, nickel-titanium alloy, a stainless steel alloy, or the like. Performance of most embodiments of the sliding seal may be enhanced with the addition of a friction-reducing surface such as a hydrophilic coating, parylene coating, or the like on the seal's mucosa-contacting surfaces. The coating or seal material itself may also be drug-eluting for targeted delivery in the esophagus.

One aspect of the intragastric implant of the invention is directed to an anchored bariatric sleeve delivery system. In one embodiment, the anchored bariatric sleeve is delivered in a compacted state, contained between an outer constraining catheter and an internal guidewire catheter. The delivery system and the gastric implant may include radiopaque markers at various points along the length of the system to aid in fluoroscopic visualization of both implant and delivery system. The radiopaque markers enable proper positioning and timing of release of various sections of the implant within the GI tract.

A preferred sequence of delivery steps for the anchored bariatric sleeve is as follows: 1) endoscopic marking of anatomical structures and guidewire placement, 2) fluoroscopic deployment of jejunal bypass sleeve, and 3) fluoroscopic placement and deployment of anchor structure in stomach.

The initial phase begins with the standard intubation of the patient with an gastroscope. As shown in FIG. 3A, under direct visualization via the gastroscope the endoscopist then creates fluoroscopic anatomy visualization aids by attaching an endoscopic clip to the mucosa of the pylorus as a marker 301 and another endoscopic clip to the mucosa of the gastroesophageal junction as a marker 302. Advancing the gastroscope past the pylorus, the endoscopist then delivers a stiff guidewire 311 into the small bowel, leaving it in place and removing the gastroscope.

Figure 3B:
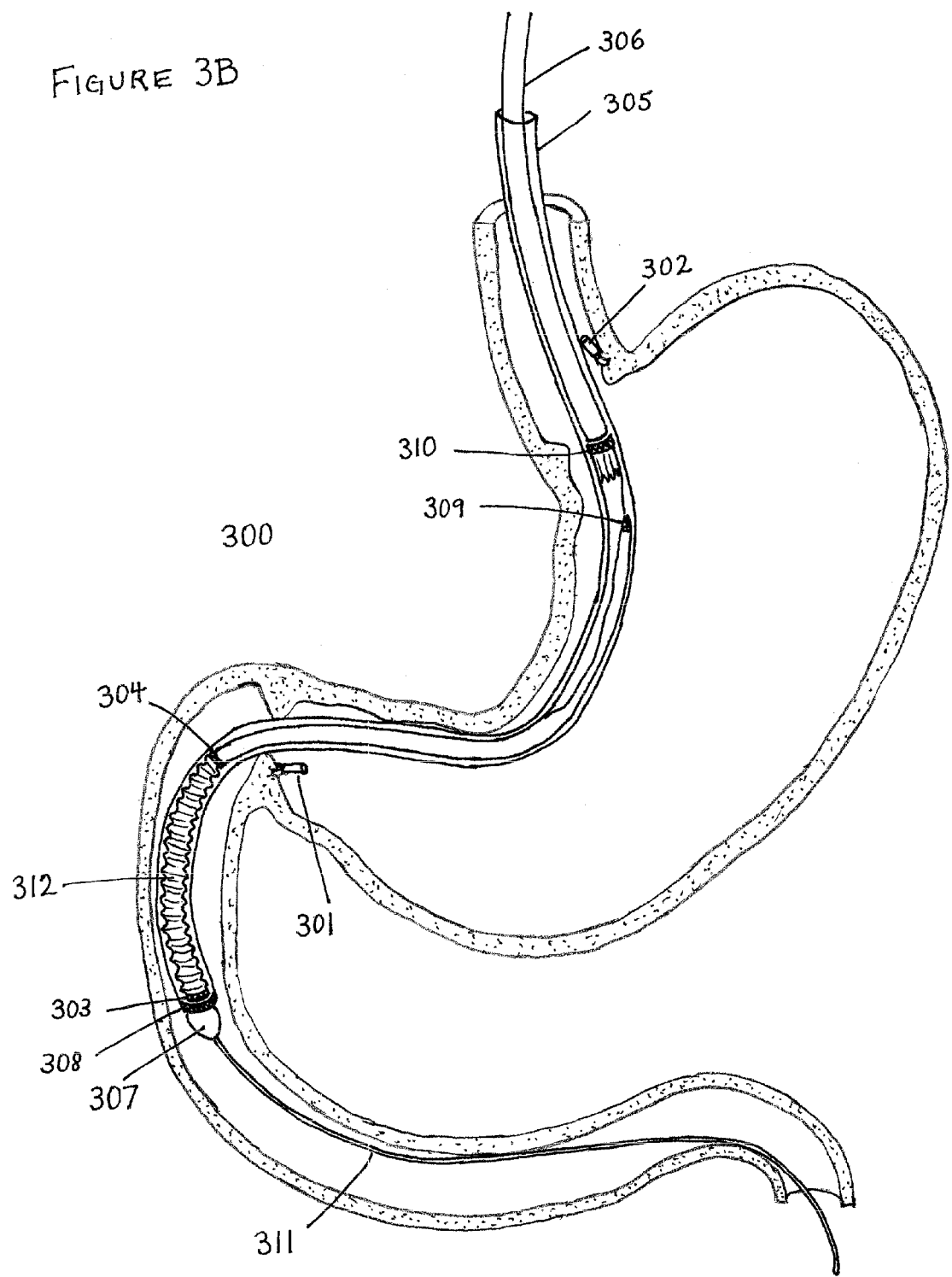
FIG. 3B is a view of a sectioned stomach and small bowel with a sheathed anchored bariatric implant on a guidewire.

Having prepared the entry path, the endoscopist switches to fluoroscopy and as shown in FIG. 3B introduces the anchored bariatric sleeve, packaged between a constraining catheter 305 and a pushing catheter 306 with a central guidewire lumen and atraumatic tip 307, into the stomach and duodenum over the guidewire, watching the fluoroscopic image to confirm that the distal sleeve marker 303 and antral bulb marker 304 have moved distally of the pylorus marker clip 301. The constraining catheter 305, visible with a distal radiopaque marker 308, is then withdrawn sufficiently to expose and release the compressed jejunal bypass sleeve 312 (approximately to the antral bulb marker 304) while the anchored bariatric sleeve is held in position by resistance from the pusher catheter 306. The guidewire is then removed and water is flushed through the guidewire lumen of the pusher catheter into the device and into the jejunal bypass sleeve 312 to help it extend past the ligament of Treitz (peristalsis can complete the job).

Following deployment of the jejunal bypass sleeve 312, the anchor portion of the anchored bariatric sleeve is positioned within the stomach by withdrawing the entire device until the antral bulb marker 304 is proximal to the pyloric marker 301 while the fundal bulb marker 309 is still distal to the gastroesophageal junction marker 302. The constraining catheter 305 is then withdrawn sufficiently to expose the fundal bulb marker 309 (but not yet releasing the device from the pusher catheter 306). Confirming that the antral bulb marker 304 is still proximal to the pyloric clip 301, the intragastric anchor is deployed such that it extends from the antrum to the fundus with the antral and fundal bulbs expanded into blunt, atraumatic shapes too large to pass through the pyloric valve. The esophageal seal, fluoroscopically visible with its own radiopaque marker 310, is then positioned in the esophagus proximal to the gastroesophageal junction clip 302 and released from the pusher 306 and constraining 305 catheters. Movement of the anchored bariatric sleeve is now constrained only by the shape of the intragastric anchor and esophageal extension.

Figure 5B:
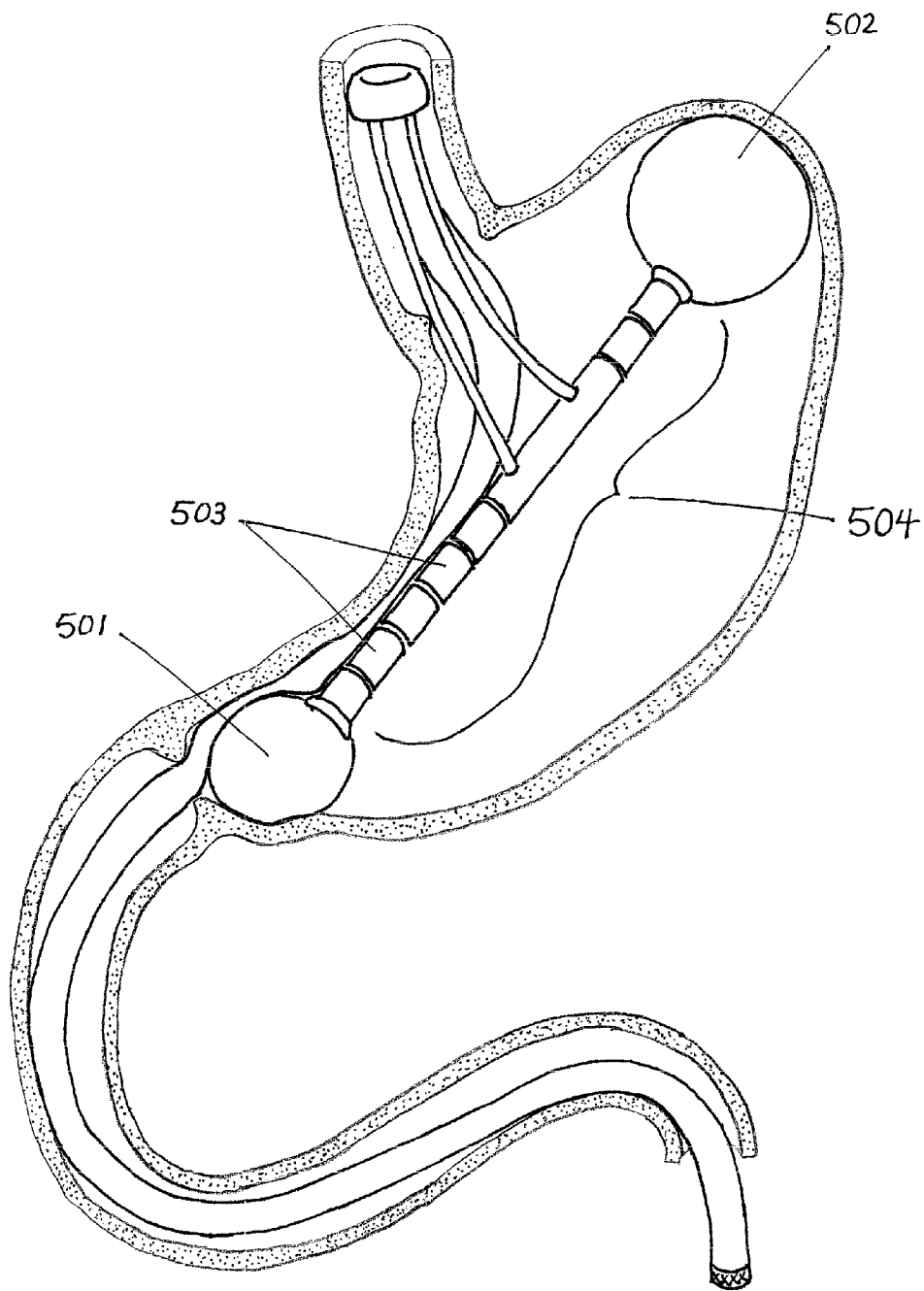
FIG. 5B is a view of a sectioned stomach with a linked intragastric anchor in a stiffened state.

An alternate embodiment of an intragastric anchor of the invention comprises a rigidizable structure. The rigidizable structure comprises links that transition between substantially flexible and substantially rigid configurations. The straightening and stiffening (rigidizing) process may be reversible or non-reversible, depending upon the design and the use for which the intragastric anchor is intended. Optionally, the rigidizable structure will further comprise a non-reversible rigid element. One example of an intragastric anchor comprising a rigidizable structure, as shown in FIGS. 5A, 5B, 5C and 5D, employs interlocking links to form a connecting shaft 500 between antral bulb 501 and fundal bulb 502. Connecting shaft 500 is configured to be reversibly substantially flexible and curved, as shown in FIG. 5A, or substantially rigid and straight, as shown in FIG. 5B. In the substantially flexible configuration, the intragastric anchor may traverse the curved path of the esophagus from the mouth to the stomach. Once converted to the substantially rigid configuration in the stomach, the intragastric anchor may support any number of therapeutic or diagnostic devices. Individual links 503 are held together by a central tether 505 which conveys tension to compress springs 508 and engage adjacent links. FIGS. 5C and 5D show an intragastric anchor having rigidizable links 503 separated by springs 508 and strung together on tether 505. In this embodiment, links 503 are configured with nestable male 506 and female 507 ends with relatively tight-fitting cylindrical sections that constrain adjacent links to a single axis when tether 505 pulls the links together. As depicted in FIGS. 5A and 5C, links 503 are normally disengaged from one another such that adjacent links may angle with respect to one another thereby imparting flexibility to the entire connecting shaft 500 linkage. As shown in FIGS. 5B and 5D, when engaged links 503 are constrained to be substantially collinear thus creating a substantially rigid connecting shaft 500. In a preferred embodiment, tether 505 may contain a central lumen used to fill an inflatable embodiment of the antral bulb 501 and fundal bulb 502. Inflation of the bulb balloons 511 and 512 as shown in FIGS. 5C (uninflated) and 5D (inflated) creates atraumatic bulb surfaces and straightens and rigidizes the structure. Bulb balloon inflation creates the tension in tether 505 required to straighten and rigidize connecting shaft 500 by retracting the tether from flared cup end links 509 and 510. In the uninflated state, flared cup end links 509 and 510 may contain compliant, pressure-expanding balloons or the flared cup end links may contain folded, pleated, or wrapped noncompliant or semi-noncompliant balloons connecting to tether 505 and configured to tension the tether when inflated. The nesting and stiffening (rigidizing) process is entirely reversible.

The specific embodiment of the bulb balloons 511 and 512 shown in FIGS. 5C and 5D contains an axial member 513 connecting opposing faces of the balloons. Axial member 513 transmits tension from the outer balloon face to the inner face and to the tether 505 when the balloon is expanded as well as serving as a location for an internal fill port 514 for the balloon. The outer end of axial member 513 may also serve as a site for a detachable pressure connection and valve 515 through which the balloons are inflated by an external source.

To prevent a linked intragastric anchor from passing into the small bowel upon an inadvertent balloon deflation or relaxation of the connecting shaft 500 and possibly causing an obstruction, a rigid element 504 as shown in FIGS. 5A and 5B and similar in function to rigid element 28 in FIG. 2, might be included in the connecting shaft or any suitable portion of the intragastric anchor. The rigid element 504 has a length dimension that is small enough to pass through the esophagus and into the stomach but is long enough not to pass beyond the duodenal bulb or through the tight bends of the relatively fixed duodenum. The rigid element 504 should normally be approximately 5 cm to 20 cm in length, preferably approximately 10 cm.

FIGS. 12A and 12B show an alternate embodiment of a linked intragastric anchor in which concentric hinged rigidizable linkages 1201 and 1202 may be shifted with respect to one another to transition the connecting shaft 1200 from a substantially flexible state to a substantially rigid state. As shown in FIG. 12A, when in the flexible state outer hinged linkage 1201 and inner hinged linkage 1202 are aligned with their respective hinges in approximately the same axial location. Spring 1203 maintains that approximate alignment by maintaining substantial contact between outer linkage shoulder 1204 and inner linkage shoulder 1205.

As is shown in FIG. 12B, inflation of tensioning balloon 1206 translates inner hinged linkage 1202 with respect to outer hinged linkage 1201 and compresses spring 1203. Putting the non-hinged portions of inner linkage 1202 inside outer hinge points 1207 and the non-hinged portions of outer linkage 1201 over inner hinge points 1208 both straightens and stiffens connecting rod 1200.

The straightening and stiffening (rigidizing) process is entirely reversible. Deflation of tensioning balloon 1206 allows spring 1203 to translate inner hinged linkage 1202 with respect to outer hinged linkage 1201, returning inner hinge points 1207 and outer hinge points 1208 to the flexible overlapping position of FIG. 12A.

Because the hinges of inner hinged linkage 1202 and outer hinged linkage 1201 must operate within approximately the same plane in order to transition from the rigid state to the flexible state, the linkages are preferably rotationally keyed to one another along their respective longitudinal axes while allowing free longitudinal sliding. This may be accomplished by employing links with a rectangular cross section or through any other suitable keying means.

Figure 7A:
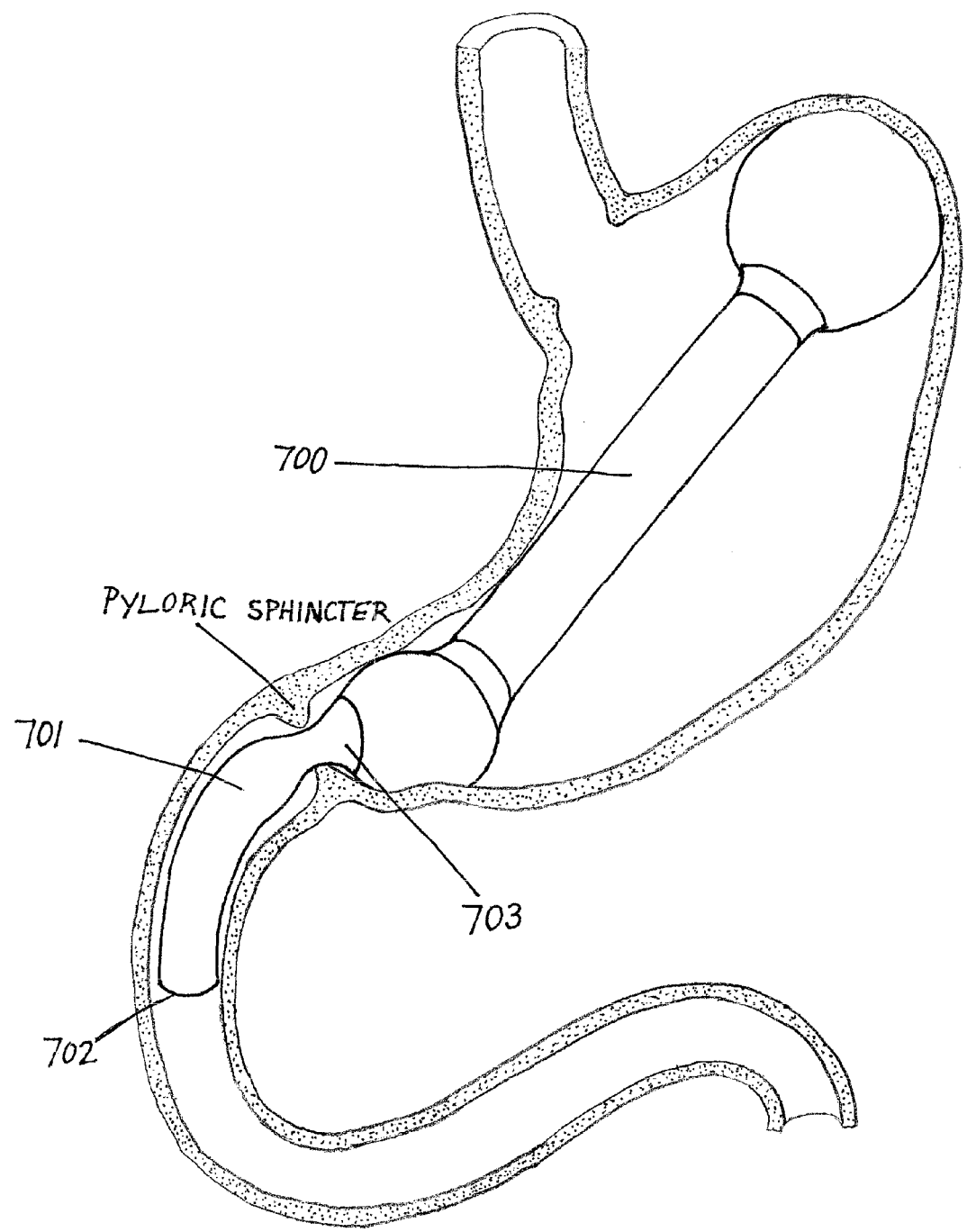
FIG. 7A is a view of a sectioned stomach with an anchored compliant gastric outflow restrictor.

Another aspect of the intragastric implant of the invention is directed to an anchored gastric outflow restrictor. As shown in FIG. 7A, an intragastric anchoring body 700 may be employed to effect delayed gastric emptying by serving as a supporting platform for a compliant gastric outflow restrictor 701. The outflow restrictor extends from the distal end of the anchoring body, though the pylorus, and into the small bowel. The outflow restrictor is configured to be compliant such that it compresses radially when the pyloric sphincter closes and expands radially when the pyloric sphincter opens, thus maintaining substantial contact with the pyloric mucosa and obstructing and limiting the exit of chyme into the duodenum from the stomach. As antral peristalsis combines with the relaxing of the pyloric sphincter, chyme must squeeze between the outflow restrictor and sphincter to exit the stomach. Thus, the compliance of outflow restrictor 701 may be tuned to allow chyme to exit the stomach at greater or lesser peristaltic pressure. The outflow restrictor 701 may be constructed in a number of different ways including but not limited to braided polymer or metallic fiber, skinned open cell elastomeric foam, silicone gel in an elongate low-durometer elastomeric container, and closely spaced radial elastomeric fins. In one presently preferred embodiment, outflow restrictor 701 is comprised of a cylindrical braided polymer mesh is embedded in a low-durometer silicone rubber to create a smooth hollow nonporous tubular structure with open end 702, a sealed proximal end 703 attached to an intragastric anchoring body 700, and an uncompressed diameter of approximately 15 mm to 35 mm, preferably approximately 25 mm. The rubber-encased braided tube may flex, expand, and compress without wrinkling or creasing, thus providing an excellent sealing surface when apposed to the pyloric sphincter. Compliance of a braided mesh outflow restrictor may be adjusted by increasing or decreasing the diameter of the braided fibers or by modifying the braid angles.

Figure 7B:
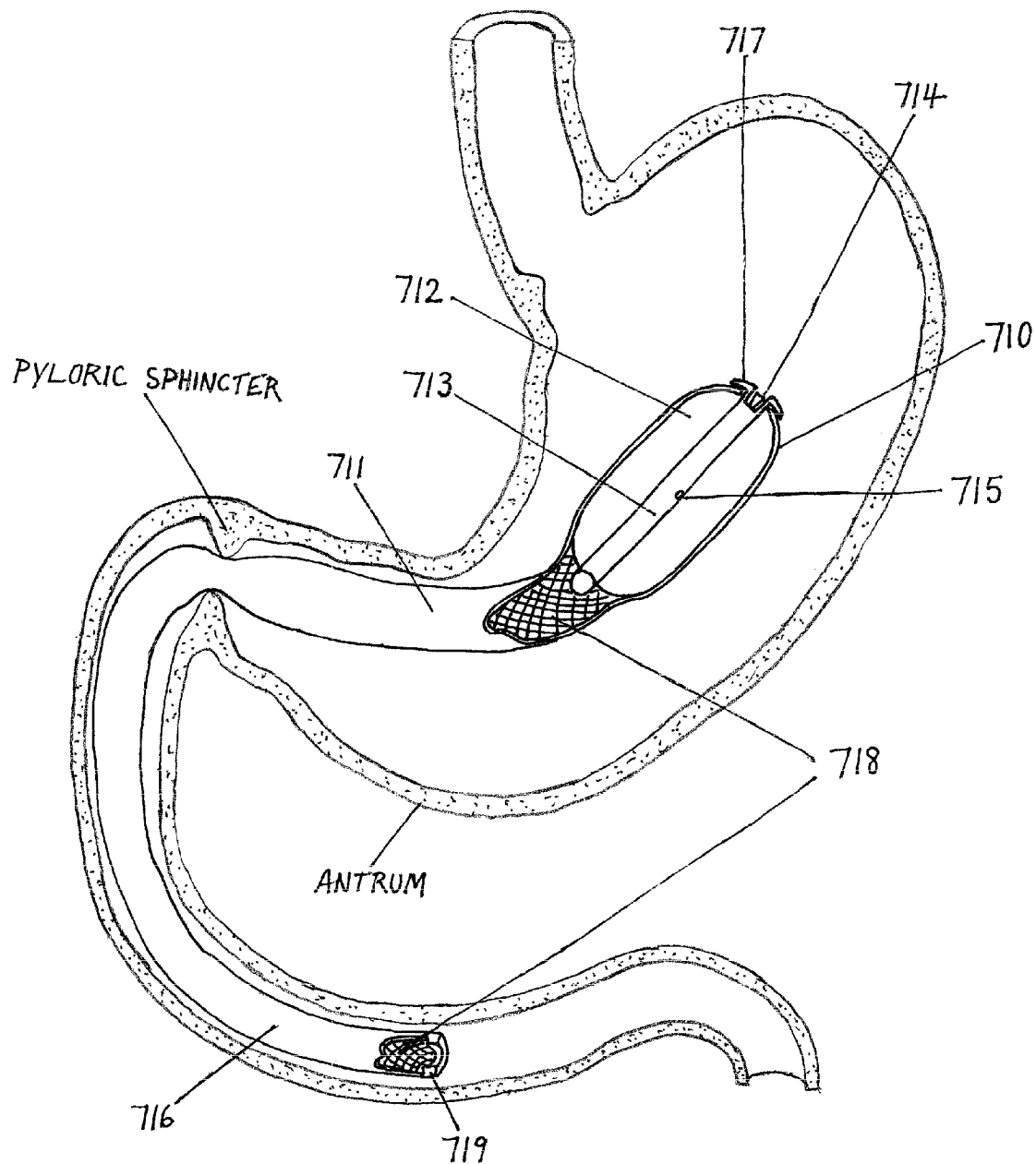
FIG. 7B is a view of a sectioned stomach with a sectioned anchored compliant gastric outflow restrictor.

FIG. 7B shows, in another embodiment, an intragastric anchor 710 supporting a compliant outflow restrictor 711. Since anchor 710 does not span the long gastric axis and, thus, can be moved out of the antrum by gastric contractility, outflow restrictor 711 is sufficiently long to maintain at least a distal portion 716 within the small bowel. Outflow restrictor 711 should normally be approximately 20 cm to 80 cm long, preferably approximately 30 cm to 50 cm, more preferably approximately 40 cm.

Within the scope of this invention, intragastric anchor 710 may be implemented as a balloon or a series of balloons, a mechanical linkage configured for radial expansion, a polymer or metallic shape-memory structure, or any suitable means. The anchor should normally have a rounded, atraumatic envelope approximately 25 mm to 50 mm in diameter, preferably approximately 35 mm in diameter, and may be spherical, oblong, cylindrical, ovoid, or any suitable shape. The anchor may include one or more deployable anchoring bodies such as balloons. By way of example, it may be advantageous to include a balloon mounted on either end of a liquid-inflated anchor's rigid element so as to reduce the overall inflated balloon volume and, thus, reduce the anchor's weight. In a presently preferred embodiment, intragastric anchor 710 is oblong in shape and comprises an assembly including a balloon 712 made of substantially noncompliant material and which substantially covers a rigid element 713 whose length dimension is small enough to pass through the esophagus and into the stomach but is long enough not to pass beyond the duodenal bulb or through the tight bends of the relatively fixed duodenum. The rigid element may also serve as an attachment point for an inflation valve 714, which may be recessed within a concealing feature 717, and as a manifold for distributing inflation fluid to one or more balloons 712 through one or more inflation ports 715. The rigid element 713 should normally be approximately 5 cm to 20 cm in length, preferably approximately 10 cm, and may be included in any suitable portion of the intragastric anchor.

In a further preferred embodiment, outflow restrictor 711 comprises a silicone rubber coated tubular braid 718 which extends over balloon 712 and terminates under a concealing feature 717, creating a smooth unbroken surface between the outflow restrictor and larger-diameter intragastric anchor 710. Tubular braid 718 may serve to limit the expansion of a compliant or semi-compliant anchor balloon 712.

Outflow restrictor 711 may include one or more relatively rigid sections 719 which resist compression by peristalsis relative to the rest of the outflow restrictor, and thus may be driven downstream in the small bowel by peristaltic contractility, thereby tending to pull the intragastric anchor distally into the antrum and against the pyloric sphincter. In a presently preferred embodiment, rigid section 719 is a section of thickened wall built up on the inner diameter of outflow restrictor 711 with silicone rubber, is located on its distal end, and serves to terminate tubular braid 718 and provide an atraumatic distal tip.

Figure 8A:
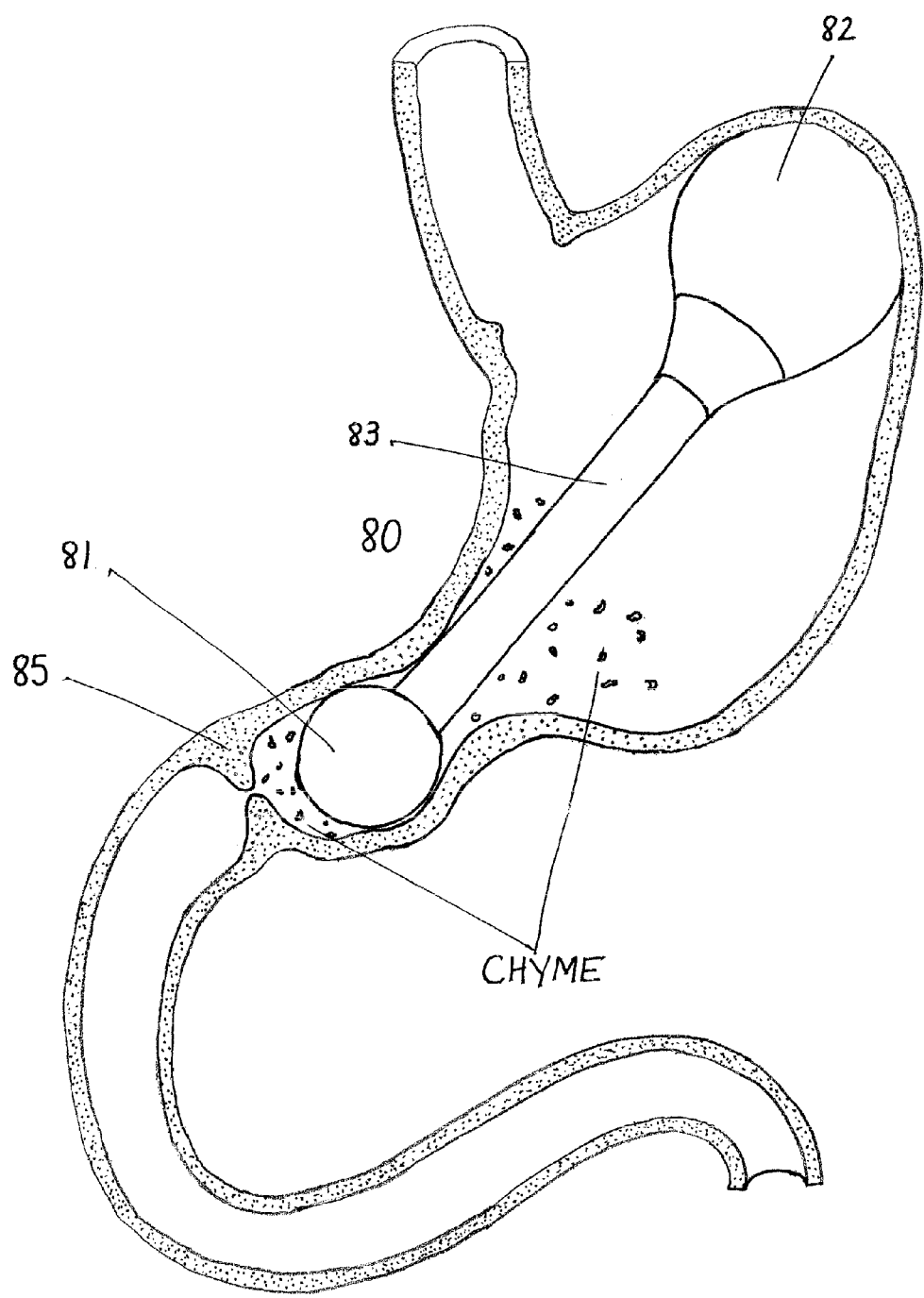
FIG. 8A is a view of a sectioned stomach with a closed pyloric sphincter and an anchored spherical gastric outflow restrictor.
Figure 8B:
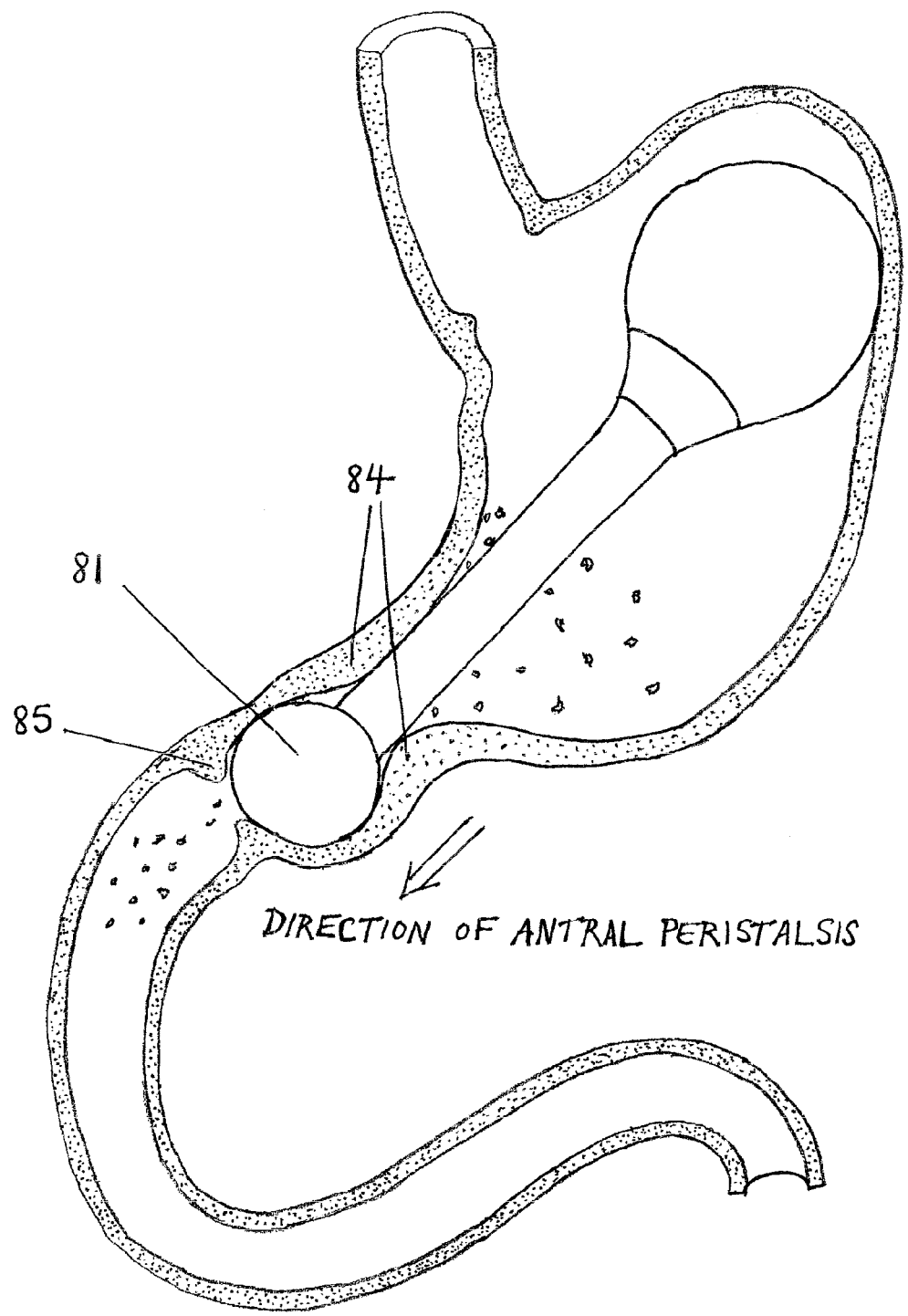
FIG. 8B is a view of a sectioned stomach with a open pyloric sphincter and an anchored spherical gastric outflow restrictor.

FIGS. 8A and 8B show an alternate embodiment of an intragastric anchor 80 supporting and locating a gastric outflow restrictor 81. The outflow restrictor diameter should normally be in the range of approximately 20 mm to 50 mm, preferably approximately 25 mm to 40 mm, more preferably approximately 30 mm, to prevent its passing through the pyloric sphincter. Fundal bulb 82 couples to connecting shaft 83 to limit the movement of the restrictor along the long axis of the stomach and away from the pylorus. As stomach contents are ground by gastric contractility and are partially digested by gastric juices as shown in FIG. 8A, the limited axial movement of the outflow restrictor 81 allows only a small amount of chyme between it and the pyloric sphincter 85. The gastric outflow restrictor is larger in diameter than the connecting shaft 83 and as shown in FIG. 8B, during gastric emptying it will be swept distally towards the open pyloric sphincter 85 by the emptying peristaltic wave 84, substantially sealing the pyloric sphincter and serving to limit the amount of chyme exiting the stomach and delaying gastric emptying.

Another aspect of the intragastric implant of the invention is directed to an anchored gastric inflow restrictor. Referring to FIG. 11, an intragastric anchoring body 112 may support a gastric inflow restrictor 110 that serves to slow the progress of oral intake from the esophagus to the stomach by reducing the effective diameter of the gastric inlet with a narrowed section 114. While narrowed section 114 may be located anywhere along the length of inflow restrictor 110, a preferred embodiment locates the narrowed section at the distal end of the inflow restrictor. Inflow restrictor 110 is normally approximately between 5 cm and 30 cm in length, preferably approximately 10 cm to 20 cm long, more preferably approximately 15 cm long. Inflow restrictor 110 is maintained in sliding contact with the esophagus overlapping the gastroesophageal junction by esophageal extension 111 which supports the inflow restrictor against anchoring body 112. Sliding seal 113 maintains a patent oral intake conduit at the proximal end of the inflow restrictor and directs most oral intake into the inflow restrictor while allowing for sliding motion proximally and distally along the esophagus as anchoring body 112 is displaced by gastric contractility and patient activity. The gastric inflow restrictor may be located entirely in the esophagus or may overlap the esophagus and stomach. The restrictor may be sufficiently compliant to compress with the closing of the lower esophageal sphincter or it may be sufficiently rigid to resist sphincter closure and at least partially stent the sphincter open.

Inflow restrictor 110 may include perforations 115 in its distal, intragastric portion to allow gastric juices to partially digest oral intake.

An intragastric anchor may support a wide range of non-bariatric therapeutic and diagnostic devices within the gastrointestinal tract. In addition to gastric inflow and outflow regulators, examples of other therapeutic devices that may be used in the present invention include, but are not limited to, drug delivery systems as are known in the art for delivering drugs directly to a targeted locale, such as the esophagus, the stomach or the small bowel (such delivery systems may be passive such as drug-eluting coatings or active such as an electronically-timed or sensor-based drug release system); radiation delivery systems for targeted radiation treatment (brachytherapy); and the like. Examples of diagnostic devices that may be used in the present invention include, but are not limited to, physiologic devices for measuring the pH in various locations in the gastrointestinal tract, for measuring the pressure differential across the lower esophageal sphincter or pyloric valve, for measuring or monitoring the secretion of digestive juices from the pancreas or the gall bladder, for measuring hormones (such as, e.g., ghrelin produced by cells lining the gastric fundus), for measuring sugars, or for measuring electrolytes, and the like; imaging probes or capsules (such as an battery-powered or inductively-powered "pill camera"); and ultrasound transducer probes (for monitoring changes in, e.g., a tumor, cyst, aortic aneurism, and the like). All of the diagnostic or therapeutic systems described may be fixed in various locations in the gastrointestinal tract (such as, e.g., the esophagus, the stomach, the jejunum, the duodenum) in the present invention by an intragastric anchor.

Figure 10:
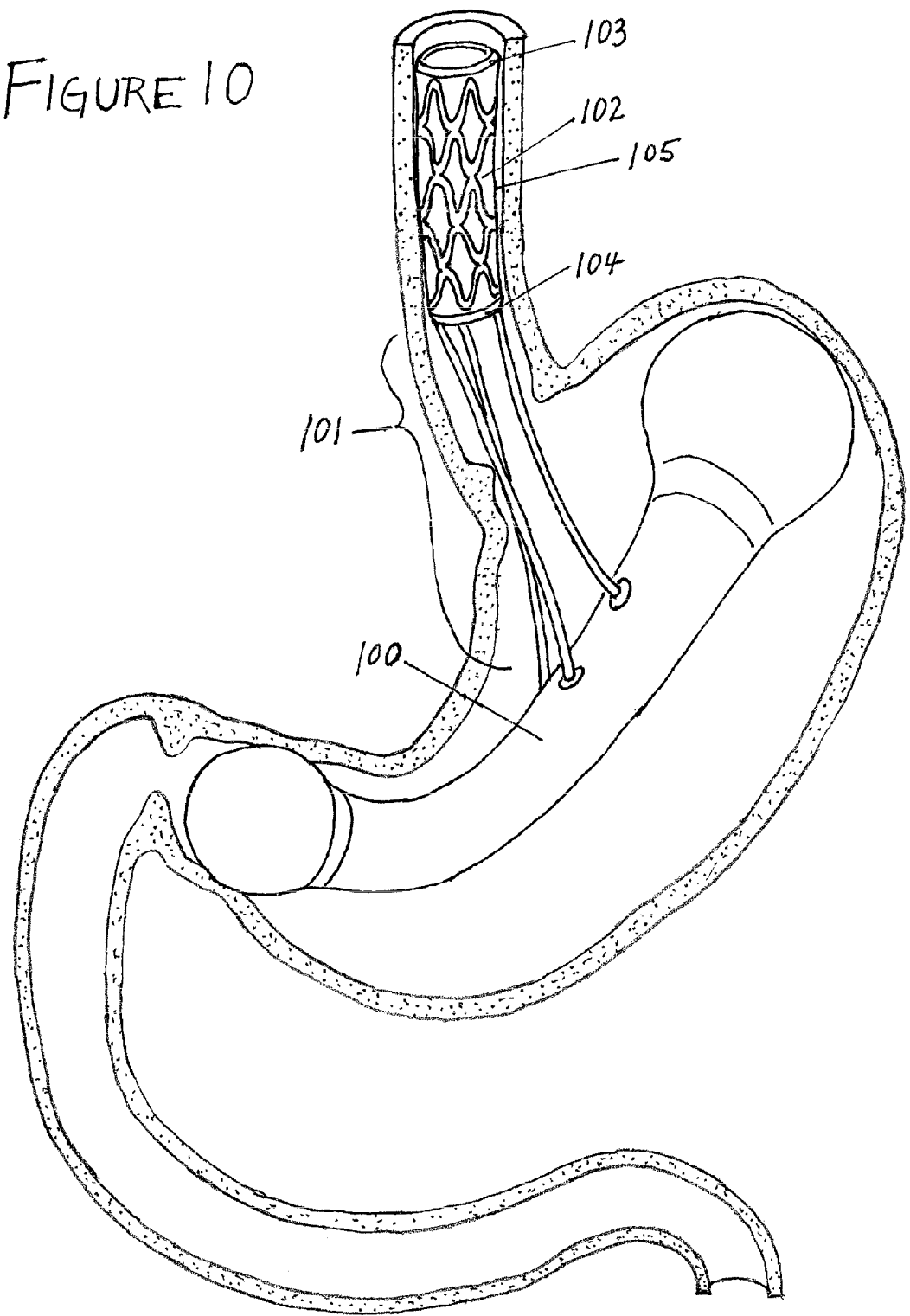
FIG. 10 is a view of a sectioned esophagus and stomach with a sliding esophageal stent supported by an intragastric anchor.

As one example, as shown in FIG. 10 an intragastric anchor 100 with esophageal extension 101 may support a removable esophageal stent 102 that is configured to allow atraumatic sliding along the esophagus so as to reduce the possibility of tissue ingrowth and minimize the pressure exerted on healthy mucosa. Sliding esophageal stent 102 may include a membrane or cover 105 to reduce the possibility of tissue ingrowth and may employ a low friction external coating such as a hydrophilic coating, parylene coating, or the like. The stent may be configured for localized drug delivery through use of a drug eluting material or coating. Similarly to the sliding seal of FIG. 6C, sliding esophageal stent 102 may include an atraumatic beveled or rounded proximal edge 103 and distal edge 104.

Figure 13:
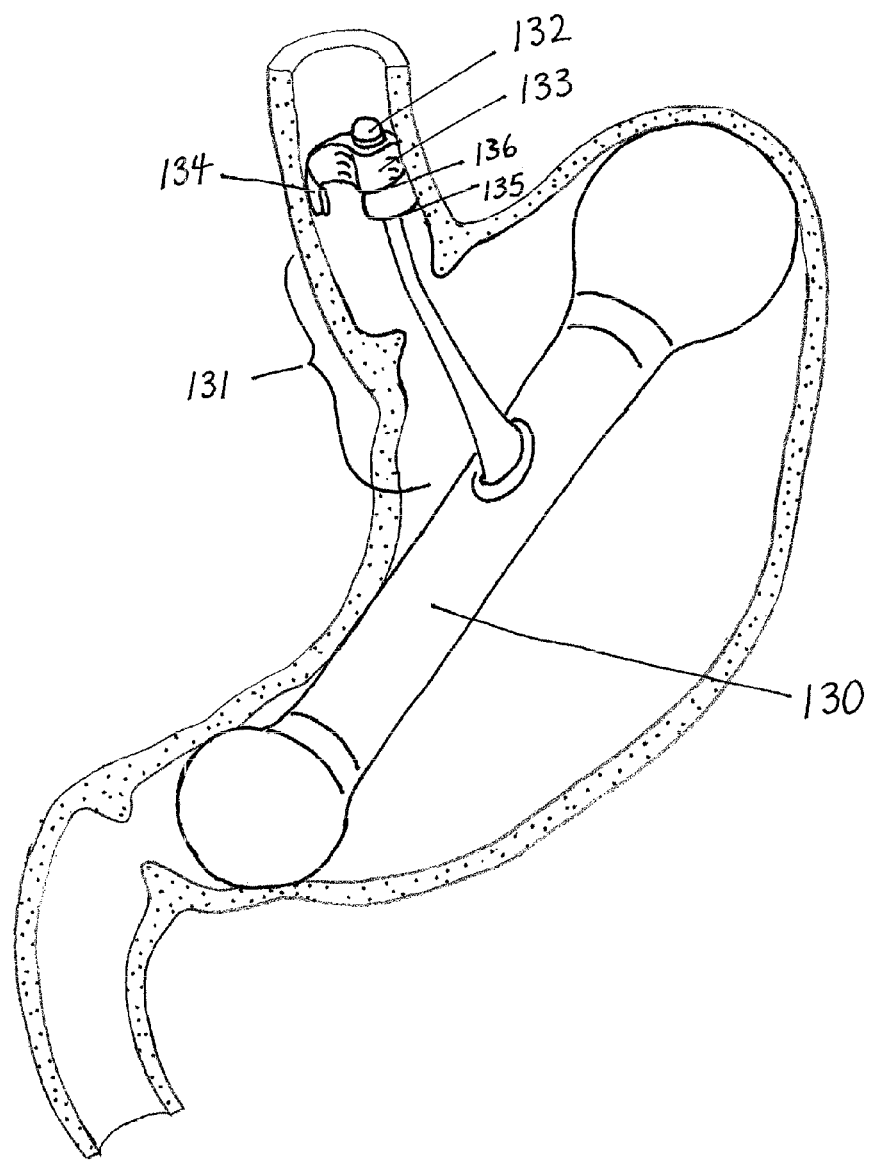
FIG. 13 is a view of a sectioned esophagus and stomach with a pH sensor and sliding apposition structure supported by an intragastric anchor.

By way of another example, as shown in FIG. 13, an intragastric anchor 130 with esophageal extension 131 may support a diagnostic device 132, such as for example a pH sensor, held substantially apposed to the esophageal wall by an atraumatic sliding apposition structure 133. The sliding apposition structure 133 provides a gentle expansion force via at least one radially compliant element 134 to allow atraumatic sliding along the esophageal wall so as to reduce the possibility of hyperplastic tissue ingrowth, minimize pressure on healthy mucosa, and enhance the removability of the sensor. Similarly to sliding stent 102, sliding apposition structure 133 may include an atraumatic beveled or rounded proximal edge 134 and distal edge 135, may include a low friction external coating such as a hydrophilic coating or parylene coating, and may be configured for localized drug delivery through use of a drug eluting material or coating. Sliding apposition structure 133 may be comprised of a unitary compliant polymer or elastomer or may include a polymer or metallic stenting structure.

What is claimed is:

1. An intragastric implant for use in a patient, the patient having an esophagus leading to a stomach, the stomach in communication with intestines through a pyloric valve, the intestines adjacent the pyloric valve including a duodenum with a duodenal bulb and bends, the intragastric implant comprising:

an intragastric anchor adapted to extend from the fundus toward the pyloric valve in the patient when deployed within the patient's gastrointestinal tract, the anchor comprising a rigid or semi-rigid elongate element having a width dimension and a length dimension, the width dimension being less than the length dimension, the elongate element being dimensioned sufficiently small to pass through the esophagus into the stomach and the length dimension being sufficiently long such that the length dimension inhibits passage of the anchor beyond the bends of the duodenum so that the anchor provides non-penetrating anchoring within the gastrointestinal tract; and an intestinal bypass sleeve coupled to the anchor, the intestinal bypass sleeve having a central passage extending from a proximal opening to a distal outlet, the distal outlet configured to be positioned in the intestines while the intragastric anchor maintains the proximal opening adjacent the stomach so that food passes through the intestinal bypass sleeve.

2. An intragastric implant as in claim 1, wherein the intragastric anchor and intestinal bypass sleeve are configured to be free from attachment to the gastric wall so that the proximal opening of the sleeve sealingly and slidably engages surrounding tissue when the intragastric anchor is disposed within the gastrointestinal tract.

3. An intragastric implant as in claim 1, wherein the intragastric anchor comprises opposing atraumatic ends including an upper atraumatic end and a lower atraumatic end when deployed within the patient's gastrointestinal tract, the rigid or semi-rigid elongate element extending along a longitudinal axis between the upper and lower atraumatic ends.

4. The intragastric implant of claim 3, wherein a diameter of one or both of the upper and lower traumatic ends is greater than a middle portion of the intragastric anchor extending therebetween.

5. An intragastric implant as in claim 3, wherein at least one of the atraumatic ends has an expandable structure that is wider than the rigid or semi-rigid elongate element when expanded so as to distribute forces exerted by longitudinal movement of the anchor.

6. An intragastric implant as in claim 1, wherein the elongate element of the anchor is rigid.

7. An intragastric implant as in claim 6, wherein the intragastric anchor is straight.

8. An intragastric implant as in claim 6, wherein the intragastric anchor is bent or curved.

9. An intragastric implant as in claim 1, wherein the intestinal bypass sleeve has a sliding seal at its proximal end supportably attached to the elongate element, wherein the sliding seal comprises a reduced friction interface adapted to slidably engage an inner wall of the gastrointestinal tract.

10. An intragastric implant as in claim 9, wherein the sliding seal is inflatable, flared, or stented.

11. An intragastric implant as in claim 9, wherein the intestinal bypass sleeve slidably extends through the pyloric valve.

12. The intragastric implant of claim 1, wherein the elongate element is dimensioned to facilitate passage through the esophagus into the stomach when rigid or semi-rigid.

13. The intragastric implant of claim 1, wherein the length dimension is sufficient to inhibit passage of the entire intragastric anchor beyond the duodenal bulb when the intragastric anchor passes through the pyloric valve.

14. The intragastric implant of claim 1, wherein the intragastric anchor is configured such that the anchor provides anchoring within the gastro-intestinal tract without penetration of or fixed attachment to tissues of the gastrointestinal tract.

15. An intragastric implant for use in a patient, the patient having an esophagus leading to a stomach, the stomach in communication with intestines through a pyloric valve, the intestines adjacent the pyloric valve including a duodenum with a duodenal bulb and bends, the intragastric implant comprising:

an intragastric anchor comprising a rigid or semi-rigid elongate element having a width dimension less than a length dimension, wherein the elongate element is dimensioned sufficiently small to pass through the esophagus into the stomach and the length dimension is sufficiently long such that the length dimension inhibits passage of the anchor beyond the bends of the duodenum so as to provide non-penetrating anchoring within the gastrointestinal tract when deployed therein without attachment to a luminal wall of the gastrointestinal tract; and a compliant cylindrical member with a distal end configured to be positioned adjacent the stomach or intestines and a proximal end configured to be positioned adjacent the stomach or esophagus.

16. An intragastric implant as in claim 15, wherein the compliant cylindrical member is a hollow tube.

17. An intragastric implant as in claim 16, wherein the hollow tube comprises a proximal opening supported by the anchor and a smooth flexible sealing surface adapted to provide a slidable seal when apposed with a mucosal wall of the gastrointestinal tract.

18. An intragastric implant as in claim 17, wherein the hollow tube comprises a gastric inflow regulator, an intestinal bypass sleeve or gastric outflow regulator and the mucosal wall comprises the esophagus, pylorus or duodenum.

19. An intragastric implant as in claim 17, wherein the slidable seal comprises a radiused or outwardly curved edge of the proximal opening to allow proximal and distal sliding when apposed against the mucosal wall.

20. An intragastric implant as in claim 17, wherein the slidable seal of the proximal opening comprises a tapered edge that tapers radially outward to allow proximal and distal sliding when apposed against the mucosal wall.

21. An intragastric implant as in claim 17, wherein the slidable seal is supported within by an expandable scaffold so as to exert an outward radial force against the mucosal wall with the smooth surface when expanded.

22. An intragastric implant as in claim 17, wherein the smooth surface comprises a hydrophilic coating to facilitate sliding against the mucosal wall.

23. An intragastric implant as in claim 17, wherein the hollow tube has an uncompressed diameter of approximately 15 mm to 35 mm to facilitate sealing by maintaining apposition between the mucosal wall and the smooth surface of the hollow tube adjacent the pylorus.

24. An intragastric implant as in claim 23, wherein the hollow tube is sized to fill an open pyloric valve.

25. An intragastric implant as in claim 16, wherein the elongate element has a length dimension sufficiently small to allow passage through the esophagus and into the stomach and sufficiently long to inhibit passage of the element beyond the duodenal bulb or through the tight bends of the relatively fixed duodenum.

26. An intragastric implant as in claim 25, wherein the length of the elongate element is between about 5 cm and about 20 cm.

27. An intragastric implant as in claim 25, wherein the length of the elongate element is about 10 cm.

28. An intragastric implant as in claim 16, the hollow tube comprises a bypass sleeve extending distally from the pylorus within the intestines.

29. An intragastric implant as in claim 28, wherein the hollow tube comprises a jejunal bypass sleeve extending from the pylorus into the jejunum.

30. An intragastric implant as in claim 16, wherein the hollow tube has proximal and distal open ends.

31. An intragastric implant as in claim 16, wherein the hollow tube is sealed closed on the proximal end so as to prevent passage of stomach contents therethrough.

32. An intragastric implant as in claim 16, wherein the hollow tube comprises a tubular braid coated with elastomer.

33. An intragastric implant as in claim 15, wherein the compliant cylindrical member is solid.

34. An intragastric implant as in claim 33, wherein the compliant cylindrical member is sized to fill an open pyloric valve.

35. An intragastric implant as in claim 15, wherein the anchor comprises a rigid element.

36. A method for treating a metabolic disorder, said method comprising:

providing an intragastric anchor coupled with an intestinal bypass sleeve, the anchor comprising an elongate element that is rigid or semi-rigid and the intestinal bypass sleeve extending from a proximal opening to a distal outlet, the proximal opening being supported by the anchor;

inserting the intragastric anchor having the rigid or semi-rigid elongate element into a stomach of a patient through an esophagus leading to the stomach, the rigid or semi-rigid elongate element being sufficiently small to facilitate passage through the esophagus into the stomach;

positioning the anchor in the stomach of the patient, the stomach being in communication with intestines through a pyloric valve, the intestines adjacent the pyloric valve including a duodenum with a duodenal bulb and bends, wherein the anchor is positioned so that the elongate element extends from the pyloric valve toward the fundus, the elongate element having a width dimension and a length dimension, the width dimension being less than the length dimension, wherein the width dimension is sufficiently small enough to pass through the esophagus into the stomach and the length dimension is sufficiently long such that the length dimension inhibits passage of the anchor beyond the bends of the duodenum so that the positioned anchor provides non-penetrating anchoring within the gastrointestinal tract without attachment to the gastrointestinal tract; and positioning a distal portion of the intestinal bypass sleeve within the duodenum so that at least a portion of the intestinal bypass sleeve extends distally from the pylorus through the duodenum.

37. A method for treating a metabolic disorder, said method comprising:

providing an intragastric anchor coupled with a hollow tube, the anchor comprising an elongate element that is rigid or semi-rigid and the hollow tube extending from a proximal opening to a distal outlet;

introducing a catheter with an internal guidewire into the stomach via the esophagus and advancing a distal atraumatic tip of the catheter through the stomach and into the duodenum;

advancing the intragastric anchor having the rigid or semi-rigid elongate element into the stomach through the esophagus within the catheter, the elongate element being rigid or semi-rigid and dimensioned sufficiently small to facilitate passage through the esophagus into the stomach;

positioning the anchor in the gastrointestinal tract of a patient so that the elongate element extends from the pyloric valve toward the fundus, wherein the elongate element has a width dimension less than a length dimension, the length dimension being sufficiently long such that the length dimension inhibits passage of the anchor beyond the bends of the duodenum providing anchoring within the gastrointestinal tract without attachment to the stomach wall; and deploying the hollow tube through the duodenum so that a proximal opening of the hollow tube is supported by the intragastric anchor and the distal opening is disposed within the intestines.

38. The method of claim 37, further comprising:

limiting absorption of food with the hollow tube by slidably sealing a smooth outer surface of the hollow tube against a mucosal wall adjacent the pylorus.

39. The method of claim 38, wherein deploying the hollow tube comprises using an intestinal bypass sleeve or gastric outflow restrictor.

40. The method of claim 38, wherein the proximal opening of the hollow tube is supported by the anchor and comprises a smooth flexible sealing surface that provides a slidable seal when apposed with a mucosal wall of the gastrointestinal tract.

41. The method of claim 40, wherein the hollow tube comprises a gastric inflow regulator, an intestinal bypass sleeve or gastric outflow regulator and the mucosal wall comprises the esophagus, pylorus or duodenum.

42. An intragastric implant for use in a patient, the patient having an esophagus leading to a stomach in communication with intestines within a gastrointestinal tract, the intragastric implant comprising:

an intragastric anchor providing anchoring within the gastrointestinal tract;

an intestinal bypass sleeve coupled to the intragastric anchor, the sleeve having a central passage extending from a proximal opening to a distal outlet, the distal outlet configured to be positioned in the intestines while the intragastric anchor maintains the proximal opening adjacent the stomach so that food passes through the intestinal bypass sleeve; and a sliding seal supportably attached to a proximal portion of the intestinal bypass sleeve so that food passes into the intestinal bypass sleeve through the proximal opening, wherein the sliding seal is adapted to slidably engage an inner wall of the gastrointestinal tract with a reduced-friction interface that facilitates sliding along the inner wall of the gastrointestinal tract and inhibiting damage thereto.

43. The intragastric implant of claim 42, wherein the sliding seal is coupled to the intragastric anchor through one or more semi-flexible struts.

44. The intragastric implant of claim 42, wherein the slidable seal comprises an expandable stent-like structure urging a slidable sealing surface radially outward against a mucosal wall of the gastrointestinal tract, wherein the slidable sealing surface comprises the reduced-friction interface.

45. The intragastric implant of claim 42, wherein the slidable seal comprises a proximal leading edge that curves radially inward so as to facilitate sliding of the sliding seal along the reduced-friction interface and inhibit trauma to the gastrointestinal tract.

* * * * *